(12) United States Patent
Tømmeraas et al.

(10) Patent No.: US 7,993,678 B2
(45) Date of Patent: Aug. 9, 2011

(54) HYALURONIC ACID DERIVATIVES

(75) Inventors: Kristoffer Tømmeraas, Bunkeflostrand (SE); Corinne Eenschooten, Vanløse (DK)

(73) Assignee: Novozymes Biopolymer A/S, Bagsvaerd (DK)

( * ) Notice: Subject to any disclaimer, the term of this patent is extended or adjusted under 35 U.S.C. 154(b) by 972 days.

(21) Appl. No.: 11/572,954

(22) PCT Filed: Aug. 26, 2006

(86) PCT No.: PCT/DK2006/000523
§ 371 (c)(1),
(2), (4) Date: Jan. 30, 2007

(87) PCT Pub. No.: WO2007/033677
PCT Pub. Date: Mar. 29, 2007

(65) Prior Publication Data
US 2009/0252810 A1    Oct. 8, 2009

Related U.S. Application Data

(60) Provisional application No. 60/721,232, filed on Sep. 27, 2005.

(30) Foreign Application Priority Data
Sep. 26, 2005   (DK) ................................ 2005 01332

(51) Int. Cl.
A61K 9/50    (2006.01)
A61K 31/728    (2006.01)
C08B 37/00    (2006.01)
A61P 27/02    (2006.01)
A61P 19/02    (2006.01)
A61P 35/00    (2006.01)

(52) U.S. Cl. ............ 424/499; 536/53; 536/55.3; 514/54
(58) Field of Classification Search ........................ None
See application file for complete search history.

(56) References Cited

U.S. PATENT DOCUMENTS 6,017,901 A * 1/2000 Khan et al. .................... 514/54
2002/0086852 A1 * 7/2002 Cantor et al. ................. 514/54

FOREIGN PATENT DOCUMENTS

| EP | 0737692 | 1/2002 |
| EP | 0893451 | 3/2005 |
| WO | WO 96/35720 | 11/1996 |

OTHER PUBLICATIONS

Shogren, Starch, 52, 2000, pp. 196-204.*
Shogren, Starch, 52, 2000. (on applicant ids dated Feb. 27, 2007).*
Otto B. Wurzburg, Modified Starches, Food Science and Technology, 1995, v. 67, pp. 67-97.
Peter C. Trubiano, Succinate and Substituted Succinate Derivatives of Starch, Properties and Use of Modified Starches, 1996, Chapter 9, pp. 131-147.
W. Jarowenko, Acetylated Starch and Miscellaneous Organic Esters, Properties and Use of Modified Starches, 1986, Chapter 4, pp. 55-77.
Shogren et al., Distribution of Octenyl Succinate Groups in Octenyl Succinis Anhydride Modified Waxy Maize Starch, Starch, 2000, v. 52, pp. 196-204.
Park et al., Effect of Octenylsuccinylation on Rheological Properties of Corn Starch Pastes, Stach, 2004, v. 56, pp. 399-406.
Chen et al., Optimizing the emulsification and sizing of alkenyl succinic anhydride, Tappi Journal, Aug. 1986, pp. 95-97.

* cited by examiner

Primary Examiner — Robert A Wax
Assistant Examiner — William Craigo
(74) Attorney, Agent, or Firm — Elias Lambiris

(57) ABSTRACT

The present invention relates to the modification of hyaluronic acid (HA) with aryl/alkyl succinic anhydrides (ASA) to produce aryl/alkyl succinic anhydride HA derivatives, to the derivatives as such, and to their applications and uses, particularly in the cosmetic and biomedical industries. The ASA-HA derivatives are expected to have interesting properties that can be used for advanced formulation (bind stronger to the skin compared to non-modified HA), possibly also in delivery systems for actives or drugs by encapsulation (nano/micro capsules) or formation of nano/micro spheres. Further, the low MW ASA-HA derivatives are expected to penetrate the skin more efficiently than non-modified HA of the same MW.

15 Claims, 13 Drawing Sheets

HYALURONIC ACID DERIVATIVES

CROSS-REFERENCE TO RELATED APPLICATIONS

This application is a 35 U.S.C. §371 national application PCT/DK2006/000523 filed Sep. 26, 2006, which claims priority or the benefit under 35 U.S.C. §119 of Danish Danish application no. PA 2005 01332 filed on Sep. 26, 2005, and U.S. provisional application No. 60/721/,232 filed on Sep. 27, 2005, the contents of which are fully incorporated herein by reference.

FIELD OF THE INVENTION

The present invention relates to the modification of hyaluronic acid (HA) with aryl- or alkyl succinic anhydride (ASA) to produce aryl/alkyl succinic anhydride HA derivatives (ASA-HA), to the ASA-HA derivatives as such, and to their applications and uses, particularly in the cosmetics and biomedical industries.

BACKGROUND OF THE INVENTION

The most abundant heteropolysaccharides of the body are the glycosaminoglycans. Glycosaminoglycans are unbranched carbohydrate polymers, consisting of repeating disaccharide units (only keratan sulphate is branched in the core region of the carbohydrate). The disaccharide units generally comprise, as a first saccharide unit, one of two modified sugars—N-acetylgalactosamine (GalNAc) or N-acetylglucosamine (GlcNAc). The second unit is usually an uronic acid, such as glucuronic acid (GlcUA) or iduronate.

Glycosaminoglycans are negatively charged molecules, and have an extended-conformation that imparts high viscosity when in solution. Glycosaminoglycans are located primarily on the surface of cells or in the extracellular matrix. Glycosaminoglycans also have low compressibility in solution and, as a result, are ideal as a physiological lubricating fluid, e.g., joints. The rigidity of glycosaminoglycans provides structural integrity to cells and provides passageways between cells, allowing for cell migration. The glycosaminoglycans of highest physiological importance are hyaluronan, chondroitin sulfate, heparin, heparan sulfate, dermatan sulfate, and keratan sulfate. Most glycosaminoglycans bind covalently to a proteoglycan core protein through specific oligosaccharide structures. Hyaluronan forms large aggregates with certain proteoglycans, but is an exception as free carbohydrate chains form non-covalent complexes with proteoglycans.

Numerous roles of hyaluronan in the body have been identified (see, Laurent T. C. and Fraser J. R. E., 1992, FASEB J. 6:2397-2404; and Toole B. P., 1991, "Proteoglycans and hyaluronan in morphogenesis and differentiation." In: Cell Biology of the Extracellular Matrix, pp. 305-341, Hay E. D., ed., Plenum, N.Y.). Hyaluronan is present in hyaline cartilage, synovial joint fluid, and skin tissue, both dermis and epidermis. Hyaluronan is also suspected of having a role in numerous physiological functions, such as adhesion, development, cell motility, cancer, angiogenesis, and wound healing. Due to the unique physical and biological properties of hyaluronan, it is employed in eye and joint surgery and is being evaluated in other medical procedures.

The terms "hyaluronan" or "hyaluronic acid" are used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

HA plays an important role in the biological organism, as a mechanical support for the cells of many tissues, such as the skin, tendons, muscles and cartilage, it is a main component of the intercellular matrix. HA also plays other important parts in the biological processes, such as the moistening of tissues, and lubrication.

HA may be extracted from the above mentioned natural tissues, although today it is preferred to prepare it by microbiological methods to minimize the potential risk of transferring infectious agents, and to increase product uniformity, quality and availability.

HA and its various molecular size fractions and the respective salts thereof have been used as medicaments, especially in treatment of arthropathies, as an auxiliary and/or substitute agent for natural organs and tissues, especially in ophthalmology and cosmetic surgery, and as agents in cosmetic preparations. Products of hyaluronan have also been developed for use in orthopedics, rheumatology, and dermatology.

HA may also be used as an additive for various polymeric materials used for sanitary and surgical articles, such as polyurethanes, polyesters etc. with the effect of rendering these materials biocompatible.

The ASA modification or derivatization is well established in the paper industry where alkyl succinic anhydrides have been used to make paper surfaces (cellulosic) more water resistant (Chen, G. C. I., Woodward, T. W. (1986) *Optimizing the emulsification and sizing of alkenyl succinic anhydride*, Tappi Journal, August, 95-97). In the food industry 2-octen-1-ylsuccinic anhydride (OSA) modified starches have been used to stabilise oil/water emulsions, e.g., low fat margarines and mayonnaises, (Jarowenko, W. (In: Properties and uses of modified starches, 1986, Ed.: O. Wurzburg) *Acetylated starch and miscellaneous organic esters*, pp 55-77). Further, the rheological properties of OSA modified starches are very different compared to non-modified starches (Park, S., Chung, M.-G., Yoo, B. (2004) *Effects of octenylsuccinylation on rheological properties of corn starch pastes*, Starch 56:399-406).

The advantages of the ASA derivatisation procedure are, e.g., that the products are non-toxic, the chemicals cheap, and the reaction is a one-step procedure (Trubiano, P C. [In: Properties and uses of modified starches, 1986, Ed.: O. Wurzburg] *Succinate and substituted succinate derivatives of starch*, pp 131-147; Wurzburg, O B. 1995. *Modified starches*, In: Food Science and Technology, Vol. 67, New York, pp. 67-97).

According to earlier studies on starches, both primary and secondary hydroxyl groups react with OSA (Shogren, R L, Viswanathan, A., Felker, F., Gross, R A (2000), *Distribution of octenyl succinate groups in octenyl succinic anhydride modified waxy maize starch*, Starch 52:196-204).

SUMMARY OF THE INVENTION

There is a need, particularly in the cosmetics and biomedical industries, for hyaluronic acid based compounds or derivatives that have certain altered characteristics as compared to non-modified HA. Properties of interest are the improved ability to stabilize foam, and the ability to blend with non-hydrophilic materials, such as is used typically in cosmetics products.

The invention provides amphiphilic HA-derivative products with properties of benefit in cosmetics or biomedical applications. These products bind more strongly to the skin so that they are not so easily washed of. The ASA-HA derivatives are also suitable for use in more advanced cosmetic or biomedical formulations, e.g. in the formation of nano/macro capsules or nano/macro spheres for delivery of active compounds or drugs. ASA-HA derivatives of lower molecular weight (MW) will penetrate the skin more efficiently than non-derivatized HA of comparable MW.

In the examples herein, hyaluronic acid (HA) was modified with alkyl/aryl succinic anhydrides (ASA) under alkaline conditions (pH>8.0) in water. The resulting products were purified (precipitation or dialysis). These purified products formed partially water-insoluble aggregates in water. A 1% solution was showed to stabilize foam (reduced surface tension+increased interfacial viscosity). $^1$H NMR spectroscopy confirmed that the chemical structure of the HA "backbone" in the resulting product was unchanged, except for the introduction of ASA half-ester groups up to a degree of substitution (DS) of about 18%.

Accordingly, in a first aspect, the invention relates to a hyaluronic acid derivative comprising 'n' repeating units and having the general structural formula (I) at pH 8-9:

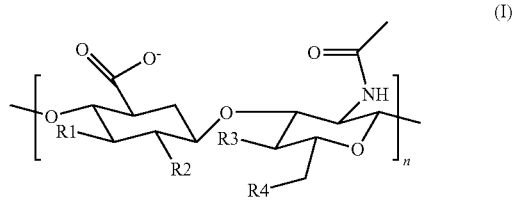

(I)

wherein in at least one repeating unit one or more of R1, R2, R3, R4 comprises an esterbound alkyl-/aryl-succinic acid having the general structural formula (II) at pH 8-9, and otherwise R1, R2, R3, R4 are hydroxyl groups, OH:

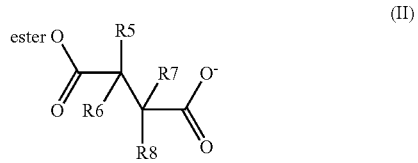

(II)

wherein at least one of R5, R6, R7, R8 comprises an alkyl- or aryl-group, and otherwise R5, R6, R7, R8 are hydrogen atoms, H, and wherein the Oxygen labelled "ester" partakes the esterbond with structure (I).

In other words, an aspect of the invention relates to a hyaluronic acid derivative, wherein one or more hydroxyl-group of the hyaluronic acid has been substituted in a reaction with one or more alkyl-/aryl-succinic anhydride (ASA), to form an ester-bond between the hyaluronic acid and the resulting one or more alkyl-/aryl-succinic acid.

In a second aspect, the invention relates to a process of producing a hyaluronic acid derivative, comprising the steps of:

(a) reacting a hyaluronic acid (HA) with one or more alkyl-/aryl-succinic anhydride (ASA) having the general structural formula shown in (III)

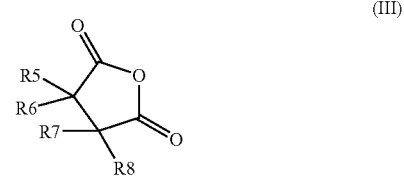

(III)

under alkaline conditions in an aqueous solution, whereby the hyaluronic acid derivative is formed; and (b) recovering the hyaluronic acid derivative.

In a third aspect, the invention relates to a composition comprising a hyaluronic acid derivative as defined in the first aspect, and an active ingredient, preferably the active ingredient is a pharmacologically active agent.

A fourth aspect of the invention relates to a pharmaceutical composition comprising an effective amount of a hyaluronic acid derivative as defined in the first aspect, together with a pharmaceutically acceptable carrier, excipient or diluent.

A fifth aspect relates to a pharmaceutical composition comprising an effective amount of a hyaluronic acid derivative as defined in the first aspect as a vehicle, together with a pharmacologically active agent.

A sixth aspect relates to a cosmetic article comprising as an active ingredient an effective amount of a hyaluronic acid derivative as defined in the first aspect or a composition as defined in any of the second, third, or fourth aspects.

In a seventh aspect, the invention relates to a sanitary, medical or surgical article comprising a hyaluronic acid derivative as defined in the first aspect or a composition as defined in any of the second, third, or fourth aspects, preferably the article is a diaper, a sanitary towel, a surgical sponge, a wound healing sponge, or a part comprised in a band aid or other wound dressing material.

An important aspect relates to a medicament capsule, microcapsule, nanocapsules, microsphere or nanosphere comprising a hyaluronic acid derivative as defined in the first aspect or a composition as defined in any of the third, fourth, or fifth aspects.

Final aspects of the invention relate to methods of performing procedures in ophthalmology, in the treatment of osteoarthritis or cancer, hair loss or baldness, of treating a wound, of performing dermal or transdermal administration of a pharmacologically active agent, or dermal administration of a cosmetic, the improvement which comprises the use of a hyaluronic acid derivative as defined in the first aspect, or a composition as defined in any of the second, third, or fourth aspects.

A number of aspects relate to uses of a hyaluronic acid derivative as defined in any of the first aspects or a composition as defined in any of the third, fourth, or fifth aspects for the manufacture of a medicament for the treatment of osteoarthritis, cancer, the manufacture of a medicament for an ophthalmic treatment, the manufacture of a medicament for the treatment of a wound, the manufacture of a medicament for angiogenesis, the manufacture of a medicament for the treatment of hair loss or baldness, or the manufacture of a moisturizer.

DETAILED DESCRIPTION OF THE INVENTION

Hyaluronic Acid

Figure 1:
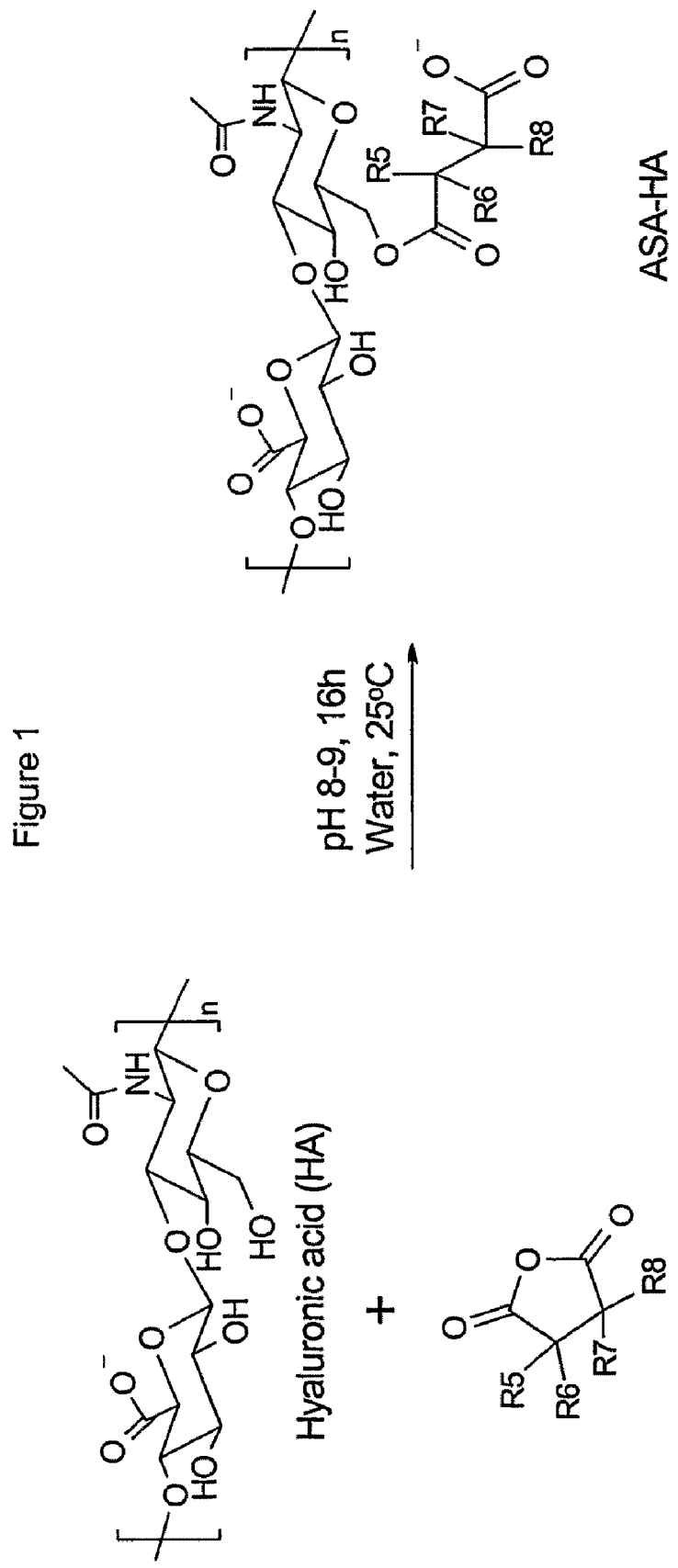
FIG. 1. The schematic ASA modification of HA is illustrated in FIG. 1.

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein.

Rooster combs are a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP0694616 discloses fermentation processes using an improved strain of *Streptococcus zooepidemicus* with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive *Bacillus* host.

Hyaluronan synthases have been described from vertebrates, bacterial pathogens, and algal viruses (DeAngelis, P. L, 1999, *Cell. Mol. Life. Sci.* 56:670-682). WO 99/23227 discloses a Group I hyaluronate synthase from *Streptococcus equisimilis*. WO 99/51265 and WO 00/27437 describe a Group II hyaluronate synthase from *Pasturella multocida*. Ferretti et al., disclose the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (*Proc. Natl. Acad. Sci. USA.* 98, 4658-4663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as spray drying.

The first aspect of the invention relates to a hyaluronic acid derivative comprising n repeating units and having the general structural formula (I) at pH 8-9:

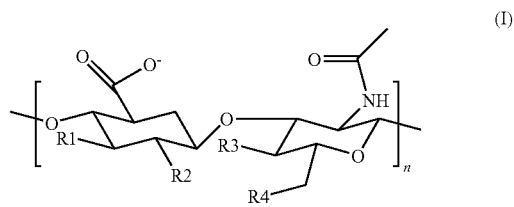

(I)

wherein in at least one repeating unit one or more of R1; R2, R3, R4 comprises an esterbound alkyl-/aryl-succinic acid having the general structural formula (II) at pH 8-9, and otherwise R1, R2, R3, R4 are hydroxyl groups, OH:

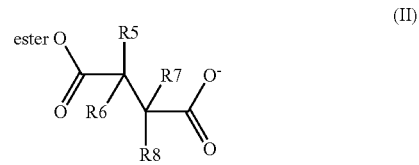

(II)

wherein at least one of R5, R6, R7, R8 comprises an alkyl- or aryl-group, and otherwise R5, R6, R7, R8 are hydrogen atoms, H, and wherein the Oxygen labelled "ester" partakes the esterbond with structure (I).

In a preferred embodiment of the first aspect, two of more of R1, R2, R3, R4 comprise one or more esterbound alkyl-/aryl-succinic acid having the general structural formula (II) at pH 8-9; preferably three or more of R1, R2, R3, R4 comprise one or more esterbound alkyl-/aryl-succinic acid having the general structural formula (II) at pH 8-9.

In another preferred embodiment of the first aspect, at least one of R5, R6, R7, R8 comprises an alkyl-group, preferably at least two of R5, R6, R7, R8 comprise an alkyl-group, more preferably at least three of R5, R6, R7, R8 comprise an alkyl-group; preferably the alkyl-group comprises a $C_1$-$C_{20}$ alkyl group, preferably propyl, 2-octenyl, 2-nonenyl, 2-dodecenyl, 2-hexadecenyl, or 2-octadecenyl.

Yet another preferred embodiment relates to the HA derivative of the first aspect, wherein at least one of R5, R6, R7, R8 comprises an aryl-group, preferably at least two of R5, R6, R7, R8 comprise an aryl-group, more preferably at least three of R5, R6, R7, R8 comprise an aryl-group; and preferably the aryl-group is phenyl.

It is preferred that R5, R6, R7, R8 comprise two or more different alkyl- and/or aryl-groups, preferably chosen from propyl, 2-octenyl, 2-nonenyl, 2-dodecenyl, 2-hexadecenyl, 2-octadecenyl, and phenyl.

Molecular Weight

The level of hyaluronic acid may be determined according to the modified carbazole method (Bitter and Muir, 1962, Anal Biochem. 4:330-334). Moreover, the average molecular weight of the hyaluronic acid may be determined using standard methods in the art, such as those described by Ueno et ah, 1988, Chem. Pharm. Bull. 36, 4971-4975; Wyatt, 1993, Anal. Chim. Acta 272:1-40; and Wyatt Technologies, 1999, "Light Scattering University DAWN Course Manual" and "DAWN EOS Manual" Wyatt Technology Corporation, Santa Barbara, Calif.

In a preferred embodiment, the hyaluronic acid derivatives obtained by the methods of the present invention has a molecular weight of about 800 to about 10,000,000 Da. In a more preferred embodiment, the hyaluronic acid derivatives obtained by the methods of the present invention has a molecular weight of about 1,000 to about 9,000,000 Da; about 2,000 to about 10,000,000 Da; about 4,000 to about 10,000,000 Da; about 8,000 to about 10,000,000 Da; about 10,000 to about 10,000,000 Da; or about 25,000 to about 5,000,000 Da. In an even more preferred embodiment, the hyaluronic acid derivatives obtained by the methods of the present invention has a molecular weight of about 50,000 to about 3,000,000 Da.

Another preferred embodiment relates to the product of the first aspect, wherein the hyaluronic acid or salt thereof has a molecular weight in the range of between 300,000 and 3,000,000; preferably in the range of between 400,000 and 2,500,000; more preferably in the range of between 500,000 and 2,000,000; and most preferably in the range of between 600,000 and 1,800,000 Da.

Where recombinantly produced hyaluronic acid or salt thereof is used in the methods of the invention to manufacture the products or compositions of the invention, it may be advantageous for some applications to first reduce the average molecular weight of the hyaluronic acid or derivative or salts thereof. For instance, it has been stated by several manufacturers of so-called low-molecular weight fractions of hyaluronic acid, that it is capable of penetrating the skin barrier to reestablish the natural content of hyaluronic acid in the skin, therefore such fractions are particularly suitable for cosmetic compositions sold as anti-skin-ageing and anti-wrinkle agents. For food applications, low MW hyaluronic acid has been shown to penetrate the gastrointestinal barrier, thereby increasing its bioavailability. Finally, low MW hyaluronic acid exhibits anti-inflammatory effect and have potential applications in the treatment of inflammatory diseases. A reduction of the average molecular weight of a hyaluronic acid or derivative or salt thereof may be achieved by standard methods in the art, such as, simple heat treatment, enzymatic degradation, ultrasound sonication, or acid hydrolysis. See, e.g., U.S. Pat. No. 6,020,484, which describes an ultrasonication technique of HA including NaOCl as additive, and T. Miyazaki et al. (2001) Polymer Degradation and Stability, 74:77-85.

Accordingly, a preferred embodiment relates to the HA derivative of the invention, wherein the hyaluronic acid or derivative or salt thereof has a low average molecular weight in the range of between 800 and 10,000,000 Da; preferably in the range of between 10,000 and 1,500,000 Da; preferably in the range of between 10,000 and 50,000 Da; or preferably in the range of between 50,000 and 500,000 Da; even more preferably in the range of between 80,000 and 300,000 Da.

Degree of Substitution (DS)

DS was determined by $^1$H NMR spectroscopy (10 mg/ml, $D_2O$, 80° C., 128 scans, 400 MHz) according to example 6 below, wherein the peaks from the OSA group were assigned by use of a 2D-NMR (gCOSY). The DS was then calculated by comparing the intensity of the vinyl protons of OSA (5.4 and 5.6 ppm) with that of the acetyl protons (2.0 ppm).

In a preferred embodiment the HA derivative of the first aspect has a Degree of Substitution (DS) in the range of 0.1-100%, preferably 1-90%, more preferably 2-80%, still more preferably 4-70%, even more preferably 8-60%, or 10-50%, 14-40%, 16-30%, or most preferably in the range of 18-25%.

Alkyl-/aryl-succinic Anhydride (ASA)

In a preferred embodiment of the invention, the one or more alkyl-/aryl-succinic anhydride (ASA) has the general structural formula (III):

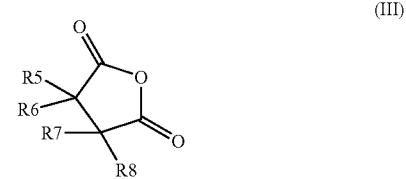

(III)

In one preferred embodiment, at least one of R5, R6, R7, R8 comprises an alkyl-group, more preferably at least two of R5, R6, R7, R8 comprise an alkyl-group, even more preferably at least three of R5, R6, R7, R8 comprise an alkyl-group; and preferably the alkyl-group comprises a $C_1$-$C_{20}$ alkyl group, preferably propyl, 2-octenyl, 2-nonenyl, 2-dodecenyl, 2-hexadecenyl, or 2-octadecenyl.

In another preferred embodiment, at least one of R5, R6, R7, R8 comprises an aryl-group, preferably at least two of R5, R6, R7, R8 comprise an aryl-group, more preferably at least three of R5, R6, R7, R8 comprise an aryl-group, which preferably comprises phenyl.

In yet another preferred embodiment R5, R6, R7, R8 comprises two or more different alkyl- and/or aryl-groups, preferably chosen from propyl, 2-octenyl, 2-nonenyl, 2-dodecenyl, 2-hexadecenyl, 2-octadecenyl, and phenyl.

Figure 3:
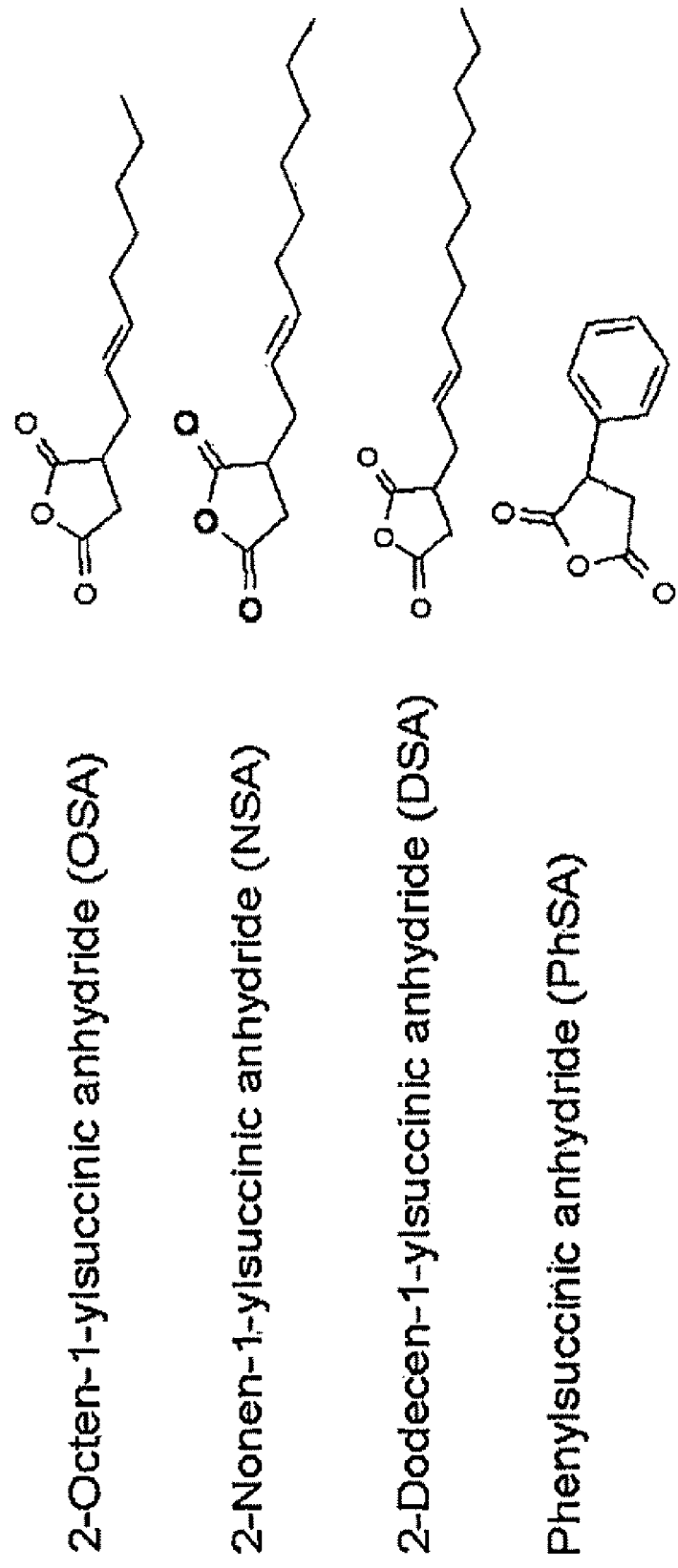
FIG. 3. The chemical structure of the ASAs used to modify HA.

In still another preferred embodiment, the one or more ASA comprises any of the structural formulae shown in FIG. 3.

Production

In the methods of the present invention recombinantly produced HA may be used that is produced by a process, wherein the HA-producing host cells are cultivated in a nutrient medium suitable for production of the hyaluronic acid using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the enzymes involved in hyaluronic acid synthesis to be expressed and the hyaluronic acid to be isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted hyaluronic acid can be recovered directly from the medium.

The resulting hyaluronic acid may be isolated by methods known in the art. For example, the hyaluronic acid may be isolated from the nutrient medium by conventional procedures including, but not limited to, centrifugation, filtration, extraction, spray-drying, evaporation, or precipitation. The isolated hyaluronic acid may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989).

Host Cells

A preferred embodiment relates to where the hyaluronic acid or salt thereof is recombinantly produced, preferably by a Gram-positive bacterium or host cell, more preferably by a bacterium of the genus *Bacillus*.

The host cell may be any *Bacillus* cell suitable for recombinant production of hyaluronic acid. The *Bacillus* host cell may be a wild-type *Bacillus* cell or a mutant thereof. *Bacillus* cells useful in the practice of the present invention include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. Mutant *Bacillus subtilis* cells particularly adapted for recombinant expression are described in WO 98/22598. Non-encapsulating *Bacillus* cells are particularly useful in the present invention.

In a preferred embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus clausii* cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164Δ5 (see U.S. Pat. No. 5,891,701) or *Bacillus subtilis* 168Δ4.

Transformation of the *Bacillus* host cell with a nucleic acid construct of the present invention may, for instance, be effected by protoplast transformation (see, e.g., Chang and Cohen, 1979, Molecular General Genetics 168:111-115), by using competent cells (see, e.g., Young and Spizizen, 1961, Journal of Bacteriology 81:823-829, or Dubnau and Davidoff-Abelson, 1971, Journal of Molecular Biology 56:209-221), by electroporation (see, e.g., Shigekawa and Dower, 1988, Biotechniques 6:742-751), or by conjugation (see, e.g., Koehler and Thorne, 1987, Journal of Bacteriology 169: 5271-5278).

Salts and Crosslinked HA

A preferred embodiment relates to a hyaluronic acid derivative of the first aspect, which comprises an inorganic salt of hyaluronic acid, preferably sodium hyaluronate, potassium hyaluronate, ammonium hyaluronate, calcium hyaluronate, magnesium hyaluronate, zinc hyaluronate, or cobalt hyaluronate.

The preparation of a crosslinked HA or salt thereof, which is prepared by crosslinking HA with a polyfunctional epoxy compound is disclosed in EP 0 161 887 B1. Total or partial crosslinked esters of HA with an aliphatic alcohol, and salts of such partial esters with inorganic or organic bases, are disclosed in U.S. Pat. No. 4,957,744. Other ways of cross-linking HA are disclosed in U.S. Pat. Nos. 5,616,568, 5,652, 347, and 5,874,417.

Crosslinked HA may also be prepared by treating HA with boric acid, as follows: Dried sodium hyaluronate (Na-HA, 203 mg), recombinantly produced in a *Bacillus subtilis* by fermentation (WO 03/054163; Novozymes), was dissolved into 0.2 M NaOH to give a 4% solution. Boric acid (35 mg (approx. 1 equivalent of HA disaccharide) was added and the sample was stirred at room temperature for 1.5 h, and then stored at 5° C. for approx. 2.5 days. A control sample was prepared in parallel exactly as described above, but without boric acid. The viscosity of the resulting HA-borate hydrogel was measured at 25° C. using a Carrimed CSL controlled stress rheometer (cone geometry: 6 cm, 2°). The viscosity depended on the shear rate and increased at least 4-fold (from 4.2- to 8.4 fold) in the HA-borate hydrogel as compared to the control sample, indicating formation of a cross-linked network. New peaks at 1200 and 945 $cm^{-1}$ were observed on the FT-IR spectrum of the HA-borate hydrogel, when compared to a standard spectrum of Na-HA, corresponding to the presence of newly formed borate esters in the crosslinked HA-borate hydrogel.

Accordingly, a preferred embodiment relates to the HA derivative of the first aspect, which comprises crosslinked hyaluronic acid or salt thereof, preferably the hyaluronic acid is crosslinked with boric acid, and more preferably the crosslinked hyaluronic acid comprises borate esters.

Particle Size

A preferred HA derivative of the first aspect has a particle size the 50 percentile of which, $D_{50}$, is between 10 and 1,000 microns, preferably between 100 and 1,000 microns, more preferably between 150 and 900 microns, and even more preferably between 200 and 800 microns, as determined by laser diffraction measurement of the particles suspended in isopropanol.

In a preferred embodiment, the polydispersity of a HA derivative of the first aspect is measured as the SPAN value, which is calculated according to the following formula: SPAN=$(D_{90}-D_{10})/D_{50}$, and the SPAN value is between 1.0 and 2.5; preferably the SPAN value is between 1.2 and 2.2; more preferably the SPAN value is between 1.5 and 1.9; and most preferably the SPAN value is between 1.6 and 1.8.

Microparticles

As shown in the examples below, the present invention provides ASA-HA derivatives that are capable of forming micro- or nanoparticles, or micro- or nanocapsules. Such particles or capsules, or compositions comprising these, may of use in a large number of commercial and scientific applications, such as in cosmetics or in general drug-delivery.

Other Ingredients

In a preferred embodiment, the compositions comprising a HA derivative of the invention may also comprise other ingredients, preferably one or more active ingredient, preferably one or more pharmacologically active substance, and also preferably a water-soluble excipient, such as lactose.

Non-limiting examples of an active ingredient or pharmacologically active substance which may be used in the present invention include protein and/or peptide drugs, such as, human growth hormone, bovine growth hormone, porcine growth hormone, growth hormone releasing hormone/peptide, granulocyte-colony stimulating factor, granulocyte macrophage-colony stimulating factor, macrophage-colony stimulating factor, erythropoietin, bone morphogenic protein, interferon or derivative thereof, insulin or derivative thereof, atriopeptin-III, monoclonal antibody, tumor necrosis factor, macrophage activating factor, interleukin, tumor degenerating factor, insulin-like growth factor, epidermal growth factor, tissue plasminogen activator, factor IIV, factor IIIV, and urokinase.

A water-soluble excipient my be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Several aspects of the invention relate to various compositions and pharmaceutical comprising, among other constituents, an effective amount of the product as defined in the first aspect, and an active ingredient, preferably the active ingredient is a pharmacologically active agent; a pharmaceutically acceptable carrier, excipient or diluent, preferably a water-soluble excipient, and most preferably lactose.

In addition, aspects of the invention relate to articles comprising a HA derivative as defined in the first aspect or a composition as defined in the aspects and embodiments above, e.g., a cosmetic article, a sanitary article, a medical or surgical article. In a final aspect the invention relates to a medicament capsule or microcapsule comprising a product as defined in the first aspect or a composition as defined in other aspects and embodiments of the invention.

EXAMPLES

Materials

High molecular weight (High-MW) Hyaluronic acid (HA):
  (batch MAG 30014)
  (batch MAF 145 SD)
Low molecular weight (Low-MW) HA:
  100 kDa (batch 14919-021)
  30 kDa (batch 14919-032)
  23 kDa
  14 kDa
Alkyl/Aryl succinic anhydrides:
  cis/trans-2-octen-1-ylsuccinic anhydride (OSA), Aldrich Chemical Company (d.: 1.000, MW 220.27, 97% purity).
  Phenylsuccinic anhydride (PhSA) (Dry powder, MW 176.17).
  Nonenylsuccinic anhydride (NSA) Aldrich Chemical Company (d.: 1.032, MW 224.30, 95+% purity, 1JS38, 246-00198-1).
  Dodecenylsuccinic anhydride (DSA) (d.: 1.01, MW 266.38, 1JS38, 246-00168).
  Tetrapropylsuccinic anhydride (TpSA).
  Hexadecenyl succinic anhydride (HDSA)
  Octadecenyl succinic anhydride (ODSA)
  Mixture (50:50) of ODSA and HDSA
Ethanol 96%, denatured.
4 M HCl, and 4 M NaOH.
$Na_2CO_3$
Milli-Q® ultrapure water (Millipore).
Dialysis tubes of regenerated cellulose with a molecular weight cutoff of 12-14 kDa, Spectr/Por™ (Spectrum Medical Industries).
Ultrafiltration membranes (MWCO 10 kDa and 3 kDa).

Example 1

High-MW OSA-HA, Initial pH 9.0, Ethanol Precipitation

HA (batch MAF 145 SD, 1.42 g) was dissolved overnight at room temperature in Milli-Q water (200 mL) before adjusting pH to 9.0 with 4 M NaOH. OSA (1 mL, 4.54 mmol) was added under strong agitation. The solution was left to react on strong agitation (approx 600 rpm) for 16 hours at ambient temperature. 20 mL saturated $NaHCO_3$ was added to buffer the reaction. After the reaction, the pH was adjusted to 6.8 with 1M HCl. The product was recovered by ethanol precipitation by adding 96% ethanol (4 volumes) to give a final concentration of 80% v/v. The precipitate was recovered by centrifugation (3000 rpm, 15 min and 4° C.). The pellet was washed with 96% ethanol before re-dissolving in MQ water and freeze drying.

Example 2

High-MW OSA-HA, Initial pH 11, Ethanol Precipitation

To each of three 50 mL solutions of Milli-Q water, HA (batch MAF 145 SD, 1.13 g) was added and left to dissolve overnight at room temperature. The pH was adjusted to 11 with 4M NaOH. Different amounts of OSA (1.10 mL (5.23 mmol), 0.505 mL (2.62 mmol), 0.110 mL (0.52 mmol)) was added to each of the three solutions under strong agitation. The solutions were left to react on strong agitation (approx 600 rpm) for 21 hours at ambient temperature. All samples had a pH of around 4-5 after the reaction. The product was recovered by ethanol precipitation by adding 96% ethanol (4 volumes) to give a final concentration of 80% v/v. The precipitate was recovered by centrifugation (3000 rpm, 15 min and 4° C.). The pellet was washed with 96% ethanol before re-dissolving in MQ water and freeze drying.

Example 3

High-MW OSA-HA, Initial pH 9.0, pH Kept at 9-11, Dialysis

HA (batch MAF 145 SD, 0.75 g) was dissolved overnight at room temperature in Milli-Q water (150 mL) before adjusting pH to 9.0. OSA (1.42 mL, 6.25 mmol) was added under strong agitation. The solution was left to react on strong agitation (approx 600 rpm) for 16 hours at ambient temperature. The pH was maintained around 9-11 by use of a pH stat (adding 1 M NaOH). The product was dialysed 3×3 h against MQ water (4° C., 7 L, MWCO 12-14,000 Da), frozen and lyophilised.

Example 4

High-MW OSA-HA, Initial pH 8.5, pH Kept at 9-11, Dialysis

HA (batch MAG 30014, 0.75 g) was dissolved overnight at room temperature in Milli-Q water (150 mL) before adjusting pH to 8.5. OSA (1.42 mL, 6.25 mmol) was added under strong agitation. The solution was left on strong agitation (approx 600 rpm) for 16 hours at ambient temperature. The pH was maintained around 9-11 by use of a pH stat (adding 1 M NaOH). pH was adjusted to 6.5 by use of 1 M HCl. The product was dialysed 3×3 h against 0.2 M NaOH, and 3×3 h against MQ water (4° C., 7 L, MWCO 12-14,000 Da), frozen and lyophilised.

Example 5

Low-MW OSA-HA (30 and 100 kDa)

Low-MW HA (30 or 100 kDa, 2.5 g) was dissolved overnight at room temperature in Milli-Q water (50 mL) before adjusting pH to 8.5. Equimolar amounts of OSA (3.35 mL, HA:OSA ratio 1:1) or 1/10 of the molar concentration of HA (0.35 mL, HA:OSA ratio 10:1) was added under strong agitation. The solution was left to react on strong agitation (approx 600 rpm) for 16 hours at ambient temperature. The pH was maintained around 8.5-9.0 by use of a pH stat (adding 1 M or 0.5 M NaOH). The product was dialysed 3×3 h against MQ water (4° C., 7 L, MWCO 12-14,000 Da), frozen and lyophilised.

Example 6

Product Characterization—Results and Discussion

Figure 2:
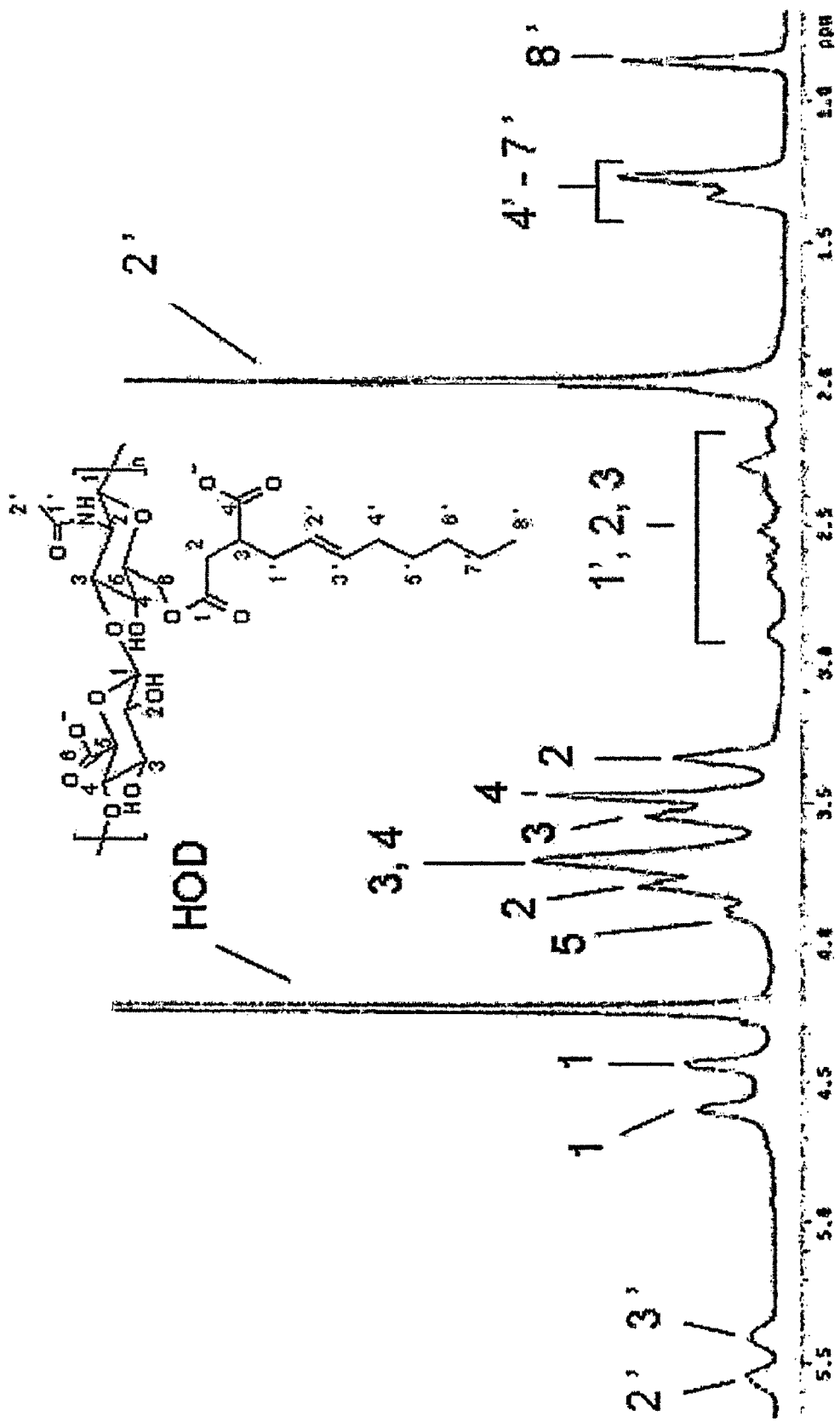
FIG. 2. The partially assigned $^1$H NMR spectrum of the 100 kDa OSA-HA (14919-033) of examples 5 and 6.

Molecular Weight
100 kDa OSA-HA from example 5 was analysed using SEC-MALLS-VISC (mobile phase: 150 mM NaCl, 50 mM $NaH_2PO_4$, pH 7.0, 0.5 ml/min, injected volume: 0.5 ml). Columns used: PL aquagel OH-40/OH-50/OH60. System: Waters Alliance HPLC system Waters 2410 RI detector and Wyatt MALLS detector. The data was processed using the ASTRA V software from Wyatt Technology Corp.
Degree of Substitution (DS)
DS was determined by $^1$H NMR spectroscopy (10 mg/ml, $D_2O$, 80° C., 128 scans, 400 MHz). The peaks from the OSA group were assigned by use of a 2D-NMR (gCOSY).
Results and Discussion; High-MW HA
During all experiments on high-MW HA the observations have been the same: OSA forms amber-coloured oil drops that gradually divide into smaller drops because of the agitation. At the end of the reaction, the solution was white and opaque like milk which can be interpreted as formation of micelles or micro-scale aggregates/droplets. Even after purification by precipitation or dialysis, where the excess of OSA is removed, this phenomenon was still observed to different extents.
During the first experiments on high-MW HA, precipitation in 80% ethanol was used to remove the surplus/by-product of the OSA modification. However, due to problems with getting the product to precipitate completely, dialysis against Milli-Q water was chosen as a better method.
The initial preparations of high-MW OSA-HA all showed changes in solution properties. One example is that they all stabilised foam very efficiently for several hours; this was simply tested by shaking a 1% solution followed by visual inspection. Another observation during the first experiments was, that the pH value of the solution declines gradually during the reaction. Therefore, it was necessary to either buffer the system, e.g., with $NaCO_3$ or by use of a pH stat. It is important, that the pH value remains above 8.0 for the reaction to proceed, and below 9.0 to avoid removing the OSA groups by hydrolysis.
NMR spectroscopy was attempted on the high-MW OSA-HA products, but because of solubility problems only some very weak peaks of OSA and HA were observed, and no DS could be determined. In all cases the yields were close or slightly higher than the amount of starting material HA (determined by weighing the lyophilized products).
Results and Discussion; Low-MW HA
Four separate experiments were performed and are summarised in Table 1 together with DS from $^1$H-NMR spectroscopy and yields. The DS is calculated by comparing the intensity of the vinyl protons of OSA (5.4 and 5.6 ppm) with that of the acetyl protons (2.0 ppm).
The $^1$H NMR spectrum of the 30 kDa OSA-HA was elucidated by 2D NMR spectroscopy (gGOSY), and the partially assigned peaks are given in FIG. 2, showing the $^1$H NMR spectrum of the 100 kDa OSA-HA (14919-033).
Conclusively, in these experiments both high- and low-MW hyaluronic acid was successfully modified with 2-octen-1-yl succinic anhydride (OSA).

TABLE 1

Results from the preparation of Low-MW OSA-HA.

| | Batch | | | | |
|---|---|---|---|---|---|
| | 14658-129 | 14658-131 | 14658-133 | 14919-033 | 14919-038 |
| HA:OSA | 1:1 | 1:1 | 10:1 | 1:1 | 10:1 |
| MW | 30 kDa | 30 kDa | 30 kDa | 100 kDa | 100 kDa |
| Yield | 2.1 g | 2.1 g | 2.8 g | 2.7 g | 2.0 g |
| DS | 11.5% | 12% | 2.6% | 18.8% | 1.6% |

Example 7

Low-MW OSA-HA Derivatives (14 kDa)

Low-MW HA (14 kDa, 2.5 g) was dissolved at room temperature in Milli-Q water (50 mL) before adjusting pH to 8.5. Equimolar amounts of OSA (3.35 mL, HA:OSA ratio 1:1) or 1/10 of the molar concentration of HA (0.34 mL, HA:OSA ratio 10:1) was added under strong agitation. The solution was left to react on strong agitation (approx 600 rpm) for 16 hours at ambient temperature. The pH was maintained around 8.5-9.0 by use of a pH stat (adding 0.5M NaOH). The product was dialysed 3×3 h against MQ water (4° C., 7 L, MWCO 12-14,000 Da), frozen and lyophilised. Yields after purification and freeze-drying were 2.1 g and 2.1 g, respectively. DS were determined as described in Example 6 to 11.5% and 2.6%, respectively.

Example 8

Low-MW Phenyl-Succinic Anhydride (PhSA) HA Derivatives (14 kDa)

Low-MW HA (14 kDa, 2.5 g) was dissolved at room temperature in Milli-Q water (50 mL) before adjusting pH to 8.5.

Equimolar amounts of PhSA (2.8 g, HA:PhSA ratio 1:1) or ¹/₁₀ of the molar concentration of HA (0.28 g, HA:PhSA ratio 10:1) was added gradually under strong agitation. The solution was left to react on strong agitation (approx 600 rpm) for 16 hours at ambient temperature. The pH was maintained around 8.5-9.0 by use of a pH stat (adding 0.5 M NaOH). The product was dialysed 3×3 h against MQ water (4° C., 7 L, MWCO 12-14,000 Da), frozen and lyophilised. Yields after purification and freeze-drying were 2.5 g and 2.4 g, respectively. DS were determined as described in Example 6 to 15.1% and 2.6%, respectively.

Example 9

Low-MW 2-nonen-1-ylsuccinic Anhydride (NSA) HA Derivatives (14 kDa)

Low-MW HA (14 kDa, 2.5 g) was dissolved at room temperature in Milli-Q water (50 mL) before adjusting pH to 8.5. Equimolar amounts of NSA (3.55 mL, HA:NSA ratio 1:1) or ¹/₁₀ of the molar concentration of HA (0.35 mL, HA:NSA ratio 10:1) was added under strong agitation. The solution was left to react on strong agitation (approx 600 rpm) for 16 hours at ambient temperature. The pH was maintained around 8.5-9.0 by use of a pH stat (adding 0.5M NaOH). The product was dialysed 3×3 h against MQ water (4° C., 7 L, MWCO 12-14,000 Da), frozen and lyophilised. Yields after purification and freeze-drying were 2.4 g and 2.2 g, respectively. DS were determined as described in Example 6 to 11.4% and 2.1%, respectively.

Example 10

Low-MW 2-dodecen-1-ylsuccinic Anhydride (DSA) HA Derivatives (14 kDa)

Low-MW HA (14 kDa, 2.5 g) was dissolved at room temperature in Milli-Q water (50 mL) before adjusting pH to 8.5. Equimolar amounts of DSA (4.20 mL, HA:DSA ratio 1:1) or ¹/₁₀ of the molar concentration of HA (0.42 mL, HA:DSA ratio 10:1) was added under strong agitation. The solution was left to react on strong agitation (approx 600 rpm) for 16 hours at ambient temperature. The pH was maintained around 8.5-9.0 by use of a pH stat (adding 0.5M NaOH). The product was dialysed 3×3 h against MQ water (4° C., 7 L, MWCO 12-14,000 Da), frozen and lyophilised. Yields after purification and freeze-drying were 2.2 g and 2.2 g, respectively. DS were determined as described in Example 6 to 2.2% and 1.7%, respectively.

Example 11

Low-MW Tetrapropylsuccinic Anhydride (TpSA) HA Derivatives (14 kDa)

Low-MW HA (14 kDa, 2.5 g) was dissolved at room temperature in Milli-Q water (50 mL) before adjusting pH to 8.5. Equimolar amounts of TpA (3.25 mL, HA:TpSA ratio 1:1) or ¹/₁₀ of the molar concentration of HA (0.33 mL, HA:TpSA ratio 10:1) was added under strong agitation. The solution was left to react on strong agitation (approx 600 rpm) for 16 hours at ambient temperature. The pH was maintained around 8.5-9.0 by use of a pH stat (adding 0.5M NaOH). The product was dialysed 3×3 h against MQ water (4° C., 7 L, MWCO 12-14,000 Da), frozen and lyophilised.

Example 12

Various Low-MW ASA HA Derivatives (14 kDa)

Eleven separate experiments were performed modifying LMW HA (14 kDa) with five different ASAs (see FIG. 3 for the ASA names, structures, and abbreviations) at two different HA:ASA molar ratios (1:1 and 10:1). The resulting products were purifies by dialysis to remove excess reagent and byproducts. The degree of substitution (DS) was determined on monomer basis by $^1$H NMR spectroscopy. Yield was determined gravimetrically the freeze dried samples. Molecular weight was determined by SEC-MALLS-VISC. To avoid material getting stuck on the GPC columns the temperature was adjusted from 4° C. to 15° C. in the auto-injector. All results from the analyses are summarised in Table 2.

TABLE 2

Results from the preparation and characterisation of ASA modified LMW HA (14 kDa starting material).

| Sample | ASA | Ratio (ASA:HA) | Degree of substitution (%) | Yield (g) | Molecular weight, $M_w$ (kDa) | Conformational plot factor; v ($R_g \sim M^v$) |
|---|---|---|---|---|---|---|
| 14658-142 | OSA | 1:1.25 | 9.7 | 2.70 | 17.0 | 0.35 ± 0.04 |
| 14658-144 | OSA | 1:0.125 | 3.5 | 2.37 | 14.2 | 0.56 ± 0.05 |
| 14658-148 | PhSA | 1:1.25 | 1.8 | 2.19 | 13.8 | 0.62 ± 0.04 |
| 15286-017[a] | PhSA | 1:1.25 | 15 | 1.80 | 15.9 | 0.67 ± 0.02 |
| 14658-150 | PhSA | 1:0.125 | 3.4 | 2.19 | 14.3 | 0.58 ± 0.02 |
| 15286-010 | NSA | 1:1.25 | 11 | 2.35 | 21.1[c] | 0.04 ± 0.02 |
| 15286-012 | NSA | 1:0.125 | 2.1 | 2.24 | 14.4 | 0.20 ± 0.01 |
| 15286-014[b] | DSA | 1:1.25 | 2.2 | 2.20 | 14.1 | 0.61 ± 0.02 |
| 15286-020[b] | DSA | 1:0.125 | 1.7 | 2.24 | 14.0 | 0.49 ± 0.02 |
| 15286-028 | TpSA | 1:1.25 | * | * | * | * |
| 15286-037 | TpSA | 1:0.125 | * | * | * | * |

[a]Repeated and downscaled version of 14658-148. PhSA was added in small portions instead of all at once.
[b]Problems with DSA - too thick to disperse efficiently with normal stirring; an oil phase was formed during dialysis that had to be removed by pipette and discarded.
[c]Bimodal distribution; peak 1: 15.5 kDa, peak2: 27.2 kDa
* Currently being analysed.

As can be seen from the results summarized in table 2, the derivatisation reaction runs smoother when a lower DS is the desired outcome. The obtained DS's are quite similar for all the different ASAs, except for the PhSA which apparently is very instable in water, resulting in a low DS value (2.19) for sample 14658-148. The experiment was repeated where the PhSA powder was added gradually to the HA-solution. This resulted, in a DS of 15% (15286-017), showing that gradual addition of the ASA could be a way of increasing the substitution on HA.

For the LMW HA modified with DSA, the DS values are also quite low at the higher ASA:HA ratio. This is probably because of the high viscosity of the DSA phase. In addition, the droplets of non-reacted ASA could still be seen after dialysis and freeze drying. This had to be removed manually by a pipette.

Probably, the DS and purity of the DSA-HA can be improved by increasing the temperature during the reaction combined with stronger agitation. Adding the DSA gradually may also increase the amount of DSA reacted with HA. The TpSA samples (15286-037 and 15286-028) have not yet been analysed yet.

Figure 4:
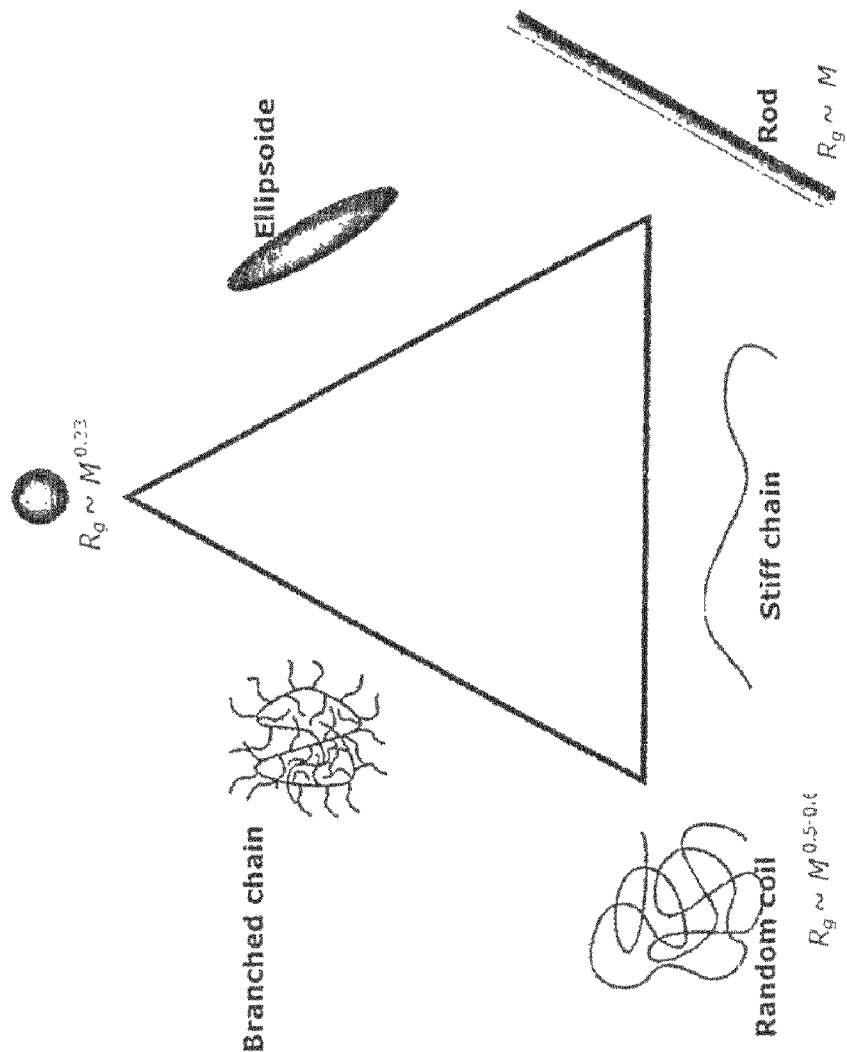
FIG. 4. Haug's triangle summarises the relationship between Rg and Mw for different polymer conformations. By plotting radius of gyration (Rg) as against molecular weight (Mw) in double logarithmic scale, one can obtain information about the conformation of the polymer.

By plotting radius of gyration (Rg) as against molecular weight (Mw) in double logarithmic scale, one can obtain information about the conformation of the polymer. The relationship Rg and Mw is summarised in Haug's triangle (FIG. 4).

Figure 5:
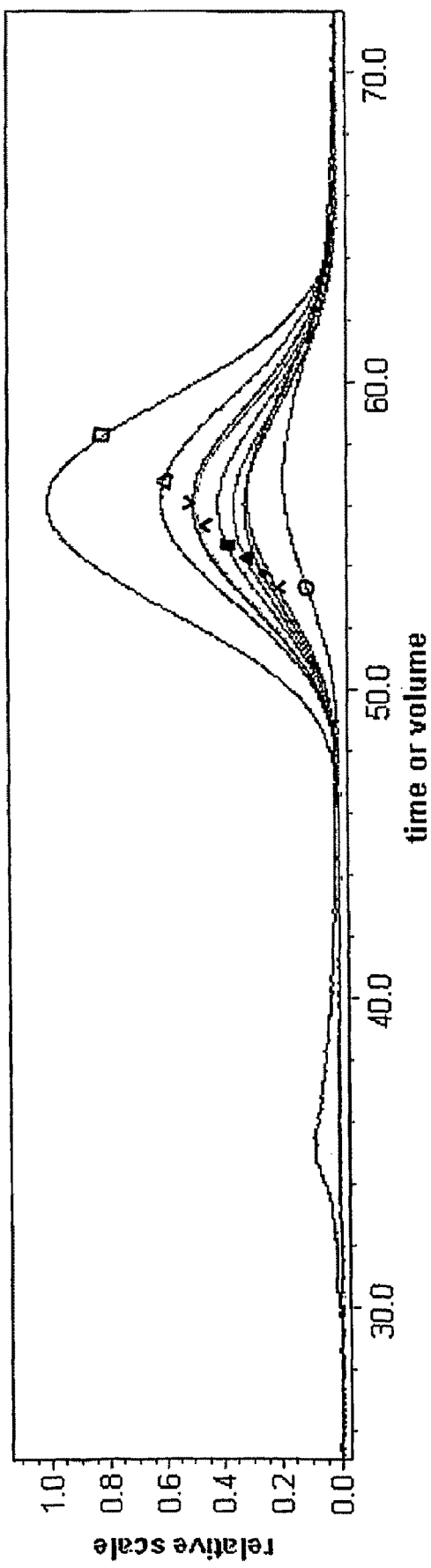
FIG. 5. Concentration profiles (RI) for the ASA modified LMW HA of example 12 below.

Conformational plots were made for all of the different ASA-HA, and the results are given in Table 2. Most of the samples show factors similar to that of random coils, which is also the conformation of non-modified HA. The only exceptions, are the highly modified OSA-HA's, which have a conformation similar to that of a sphere, and the NSA-HA's that also show very low conformational factors (0.20 and 0.04) indicating aggregation or impaired column separation, perhaps because of interactions with the column material. Similarly, looking at the concentration profile (RI-signal) from the SEC-MALLS-VISC analysis (See FIG. 5), there is an aggregation peak at an earlier elution time, at approx. 35 min, for sample 15286-010 (11% NSA). This aggregation phenomenon is also indicated by the slight increase in the apparent MW (Table 2) for samples 14658-142 (9.7% OSA modified HA) and 15286-010 (11% modified NSA-HA).

In conclusion, low MW hyaluronic acid (14 kDa) was successfully modified with diverse aryl-/alkyl succinic anhydrides. High DS products of OSA-HA and NSA-HA show some aggregation tendencies and changes in conformation, probably caused by hydrophobic interactions.

Example 13

Surface Activity of OSA-HA (14 kDa) in Aqueous Solution

Figure 6:
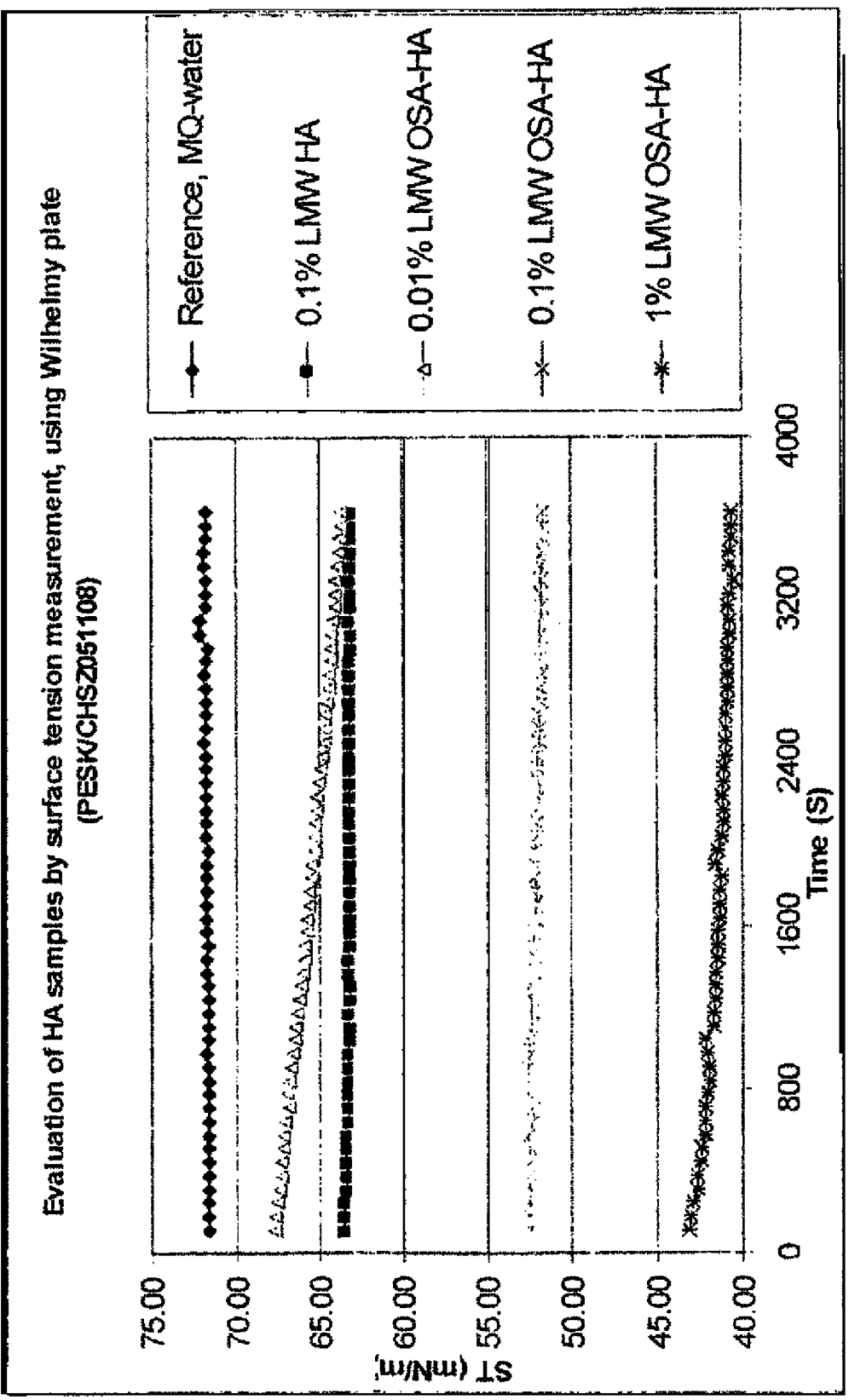
FIG. 6. Results of surface tension measurements on LMW OSA-HA using surface tensiometer (Wilhemy plate) as described in example 13.

Solutions of 14 kDa OSA-HA (DS= 9.7%, batch 14658-142) and unmodified LMW HA (30 kDa) were prepared in MQ-water according to the concentrations given in Table 3. The samples were analysed by surface tension measurements using a surface tensiometer (Wilhelmy plate). Surface tension of the solvent (water) was determined to 72 mN/m with the same method. Results of the surface tension measurements are given in FIG. 6 and summarized in Table 3. As can be seen, the surface tension decreases with increasing concentration of OSA-HA. Comparing with the pure solvent (MQ-water) and LMW-HA (30 kDa), the surface tension is much lower for the HA derivatives.

Further, it can be seen that the surface tension continues to decrease in a time dependant manner for the OSA-HAs. This can be explained by the fact that OSA-HA works as a high MW surfactant, using long time to diffuse to the surface of the solution (since diffusion speed is inversely proportional to MW). More surface active polymer at the surface gives lower surface tension. This time dependence is also a further proof of the OSA moieties actually being covalently bound to the HA, and not only co-existing with HA in the solution.

This further implies that OSA modification of HA is not rendering it hydrophobic, but amphiphilic. These properties can potentially be exploited in systems where lower surface tension is needed (e.g., local ophthalmic) or where emulsifying properties are needed to stabilise emulsions or foams in cosmetics or pharmaceutical formulations.

TABLE 3

Surface tension measurements of OSA-HA solutions in MQ-water at 3200 seconds.

| Concentration (%) | LMW OSA-HA (14 kDa, DS = 9.7%) | LMW HA (30 kDa) |
|---|---|---|
| 0.01 | 64 mN/m | — |
| 0.1 | 52 mN/m | 64 mN/m |
| 1.0 | 40 mN/m | — |

Example 14

Preparation of High MW ASA Derivatives by High Shear Mixing

HA (4 g, MAG30021) was dissolved overnight in 400 mL MQ water. Solutions were kept at room temperature (25° C.) or heated to 60° C. before $Na_2CO_3$ (2 g) was added under shear (ULTRA-TURRAX 24 000 $min^{-1}$, 5 min). Then the ASA was added according to reaction scheme presented in Table 4 and mixed under strong shear (ULTRA-TURRAX 24 000 $min^{-1}$, 5 min). The resulting emulsions were left to react for 6 hours at the given temperature (Table 4), then removed to room temperature over night. The pH was adjusted to neutrality before the products were purified by ultrafiltration (MWCO 10 000) until conductivity was below 15 μSi/cm. The products were frozen and lyophilised. NMR spectroscopy confirmed that all the products were modified. Sample all samples gave turbid solutions in 0.1 M NaCl at 1% w/v concentration.

TABLE 4

Reaction Scheme for preparation of high MW ASA-derivatives

| Sample ID | ASA | Carbon chain | ASA:HA Molar ratio | Reaction temp. [° C.] |
|---|---|---|---|---|
| 1 | OSA | C8 | 1:1 | 25 |
| 2 | OSA | C8 | 1:10 | 25 |
| 3 | ODSA | C18 | 1:1 | 60 |
| 4 | ODSA | C18 | 1:10 | 60 |
| 5 | HDSA | C16 | 1:1 | 60 |
| 6 | DSA | C12 | 1:1 | 60 |
| 7 | DSA | C12 | 1:10 | 60 |

ODSA: Octadecenyl succinic anhydride,
HDSA: Hexadecenyl succinic anhydride,
DSA: Dodecenyl succinic anhydride.

Example 15

ASA HA Stabilises O/W Emulsions

The ASA-HAs no. 1, 3, 4, 5, 6, 7, and non-modified HA (MAG30014), prepared in example 14 were formulated with three cosmetic oils (mineral oil, diethylhexyl carbonate and ethylhexyl palmitate) according to the following recipe:
1. 6 mL oil was added to 14 mL aqueous solution of 0.1 M NaCl and 0.29% ASA-HA
2. The solution was mixed under strong shear for 25 seconds (ULTRA-TURRAX at 24 000 $min^{-1}$).
3. The emulsions were left at room temperature in the dark for 8 weeks, being evaluated visually after 24 hour and 8 weeks for stability.

Figure 7:
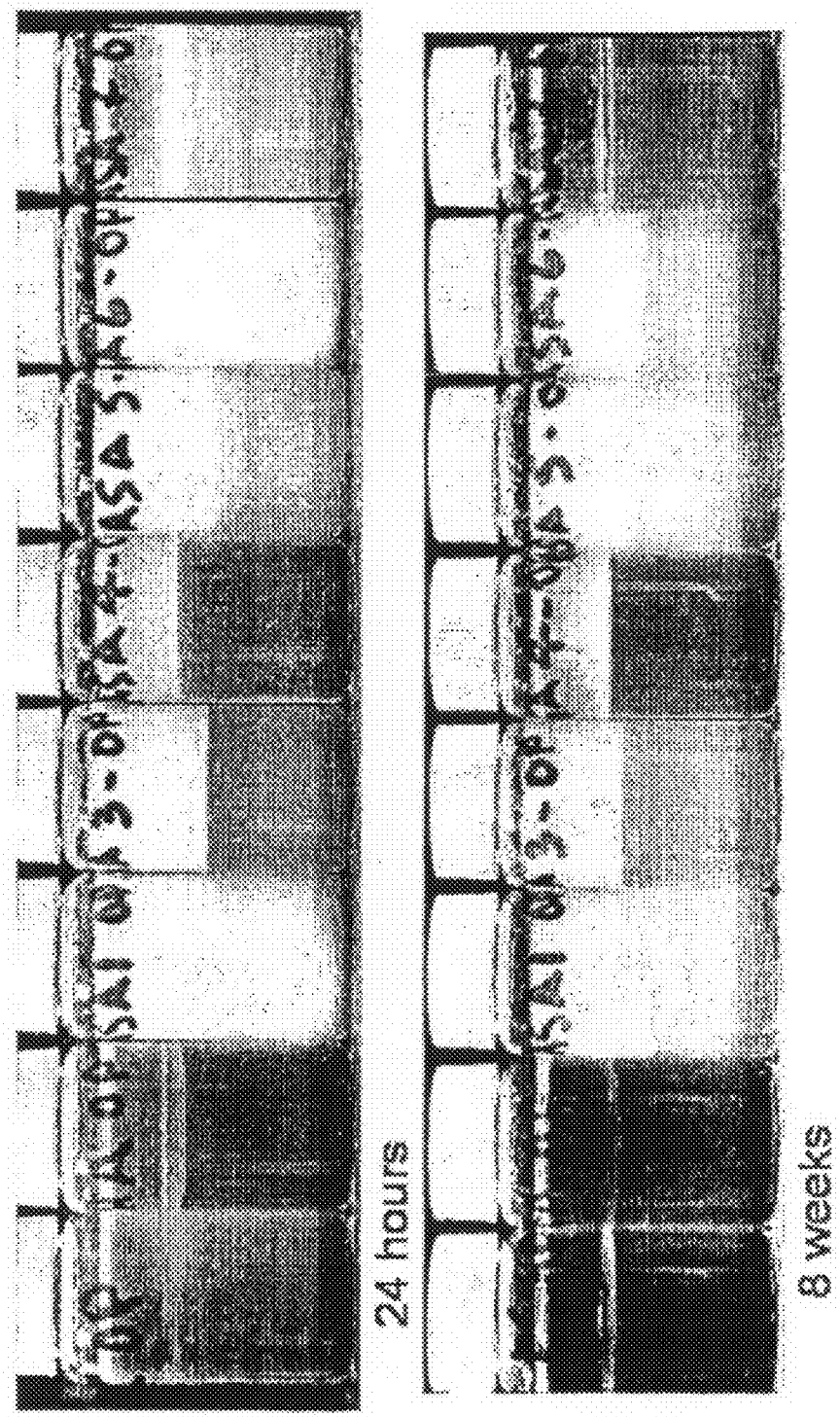
FIG. 7. Shows the emulsification properties of ASA-HA after 24 hours and 8 weeks with ethylhexyl palmitate (cosmetic oil) prepared as described in example 15

All derivatives showed increased emulsion stability compared to the control and the non-modified starting HA (see FIG. 7 for samples after 24 hour and 8 weeks for ethylhexyl palmitate). This shows that ASA-HA can be used as emulsifiers in cosmetics or advanced drug delivery systems based on emulsions.

Example 16

Various low-MW ASA HA Derivatives with Long Alkyl Chains

Low MW ASA HA was prepared as described in example 15 for high MW HA, the only difference being that the starting concentrations of HA (23 kDa) were 2% w/v. All samples in Table 5 were prepared at 60° C. and purified by ultrafiltration (MWCO 3000 kDa) and lyophilization. The DS were determined by $^1$H NMR spectroscopy as described in example 6.

TABLE 5

Reaction scheme for preparation of low MW HA derivatives with longer alkyl chains.

| Sample # | ASA | Ratio (HA/ASA) | DS (NMR spectroscopy) | Yield |
|---|---|---|---|---|
| 15286-109-1 (HA: 23 kDa) | DSA | 1:1.25 | 2.12% | 4.09 g |
| 15286-109-2 (HA: 23 kDa) | DSA | 1:0.125 | Confirmed modified | 3.44 g |
| 15286-118-1 (HA: 23 kDa) | HDSA/ODSA (50:50) | 1:1.25 | 13.14% | 6.73 g |
| 15286-118-2 (HA: 23 kDa) | HDSA/ODSA (50:50) | 1:0.125 | 1.06% | 3.84 g |
| 15286-120-1 (HA: 23 kDa) | ODSA | 1:1.25 | 12.94% | 6.15 g |
| 15286-120-2 (HA: 23 kDa) | ODSA | 1:0.125 | 0.08% | 2.96 g |

Example 17

Free Radical Scavenging Properties of Phenyl Succinic Acid

PhSA-HA (14 kDa) (10 mg/ml) in aqueous solution has been shown to degrade much faster than non-modified HA in the presence of hydroxyl radicals (generated by $Cu^{2+}/H_2O_2$) followed by both streak camera observations and light scattering (DLS/SLS) studies. This shows that PhSA-HA has a potential as a free-radical scavenging agent for potential use in cosmetic formulations.

Example 18

Determination of Critical Aggregation Concentration (CAC) of Octenyl Succinic Anhydride-hyaluronic Acid Derivative (OSA-HA, DS 16%)

Figure 8:
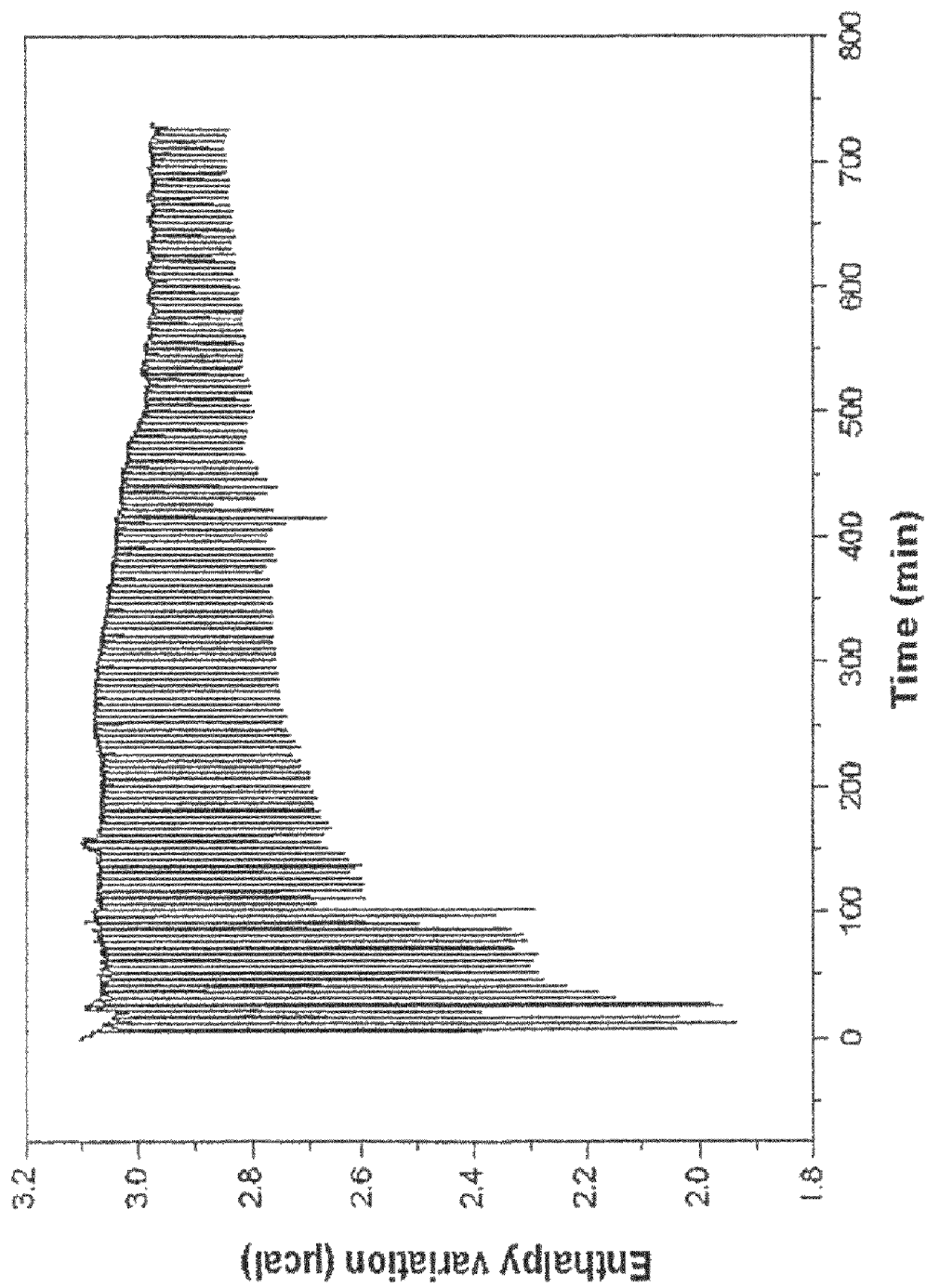
FIG. 8. The critical aggregation concentration (CAC) of an OSA-HA derivative was determined by calorimetry as described in Example 18, enthalpy variations ($\Delta$H) in the sample cell were recorded over time as shown in FIG. 8.

The critical aggregation concentration (CAC) of an OSA-HA derivative was determined by calorimetry using an isothermal titration calorimeter VP-ITC (Microcal LLC, USA). A concentrated solution of OSA-HA (0.294 mL, 15 mg/mL in distilled water) was used to titrate distilled water (1.4615 mL) in the calorimeter sample cell. A solution of OSA-HA (2 μL, 15 mg/mL) was injected every 300 seconds, and enthalpy variations (ΔH) in the sample cell were recorded over time as shown in FIG. 8.

Figure 9:
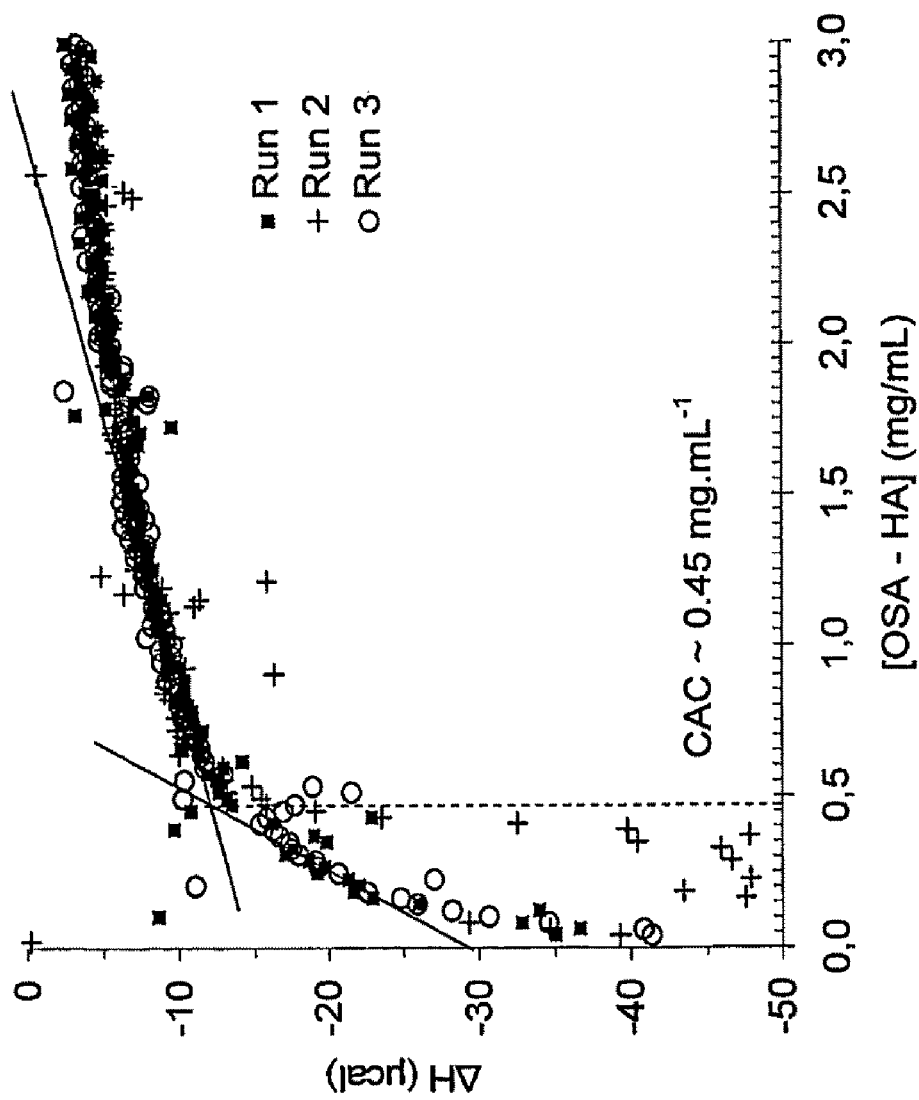
FIG. 9. Enthalpy variation ($\Delta$H) of Example 18 was plotted as a function of the OSA-HA concentration in the sample cell, and the CAC of OSA-HA was determined at the break of the curve. Each experiment was repeated three times and the CAC was provided as an averaged value. For example, the CAC of OSA-HA with a degree of substitution (DS) of 16% was 0.45 mg/mL.

ΔH was plotted as a function of the OSA-HA concentration in the sample cell, and the CAC of OSA-HA was determined at the break of the curve. Each experiment was repeated three times and the CAC was provided as an averaged value. For example, the CAC of OSA-HA with a degree of substitution (DS) of 16% was 0.45 mg/mL (FIG. 9).

This study confirmed the existence of associative properties of OSA-HA. Moreover, it indicated the potential formulation of these derivatives into micelles and/or micro-/nano-particles, making them suitable for use in the encapsulation and delivery of hydrophobic compounds such as hydrophobic cosmetic bioactives and drugs.

Example 19

Determination of Critical Aggregation Concentration (CAC) of Octenyl Succinic Anhydride-hyaluronic Acid Derivative (OSA-HA, DS 44%)

The CAC of OSA-HA with a degree of substitution of 44% was determined by fluorescence spectroscopy using a spectrofluorimeter (FluoroMax, Spex, United States) thermostated with a water bath (Julabo F10, Merck, United States). Nile Red was employed as the fluorescent probe. Fluorescence was measured on a range of OSA-HA solutions (Table 6) prepared in different phosphate buffers (Table 7).

TABLE 6

OSA-HA solutions

| Solution | Concentration OSA-HA (mg/mL) |
|---|---|
| 1 | 0.0001 |
| 2 | 0.0002 |
| 3 | 0.0006 |
| 4 | 0.001 |
| 5 | 0.002 |
| 6 | 0.006 |
| 7 | 0.01 |
| 8 | 0.02 |
| 9 | 0.06 |
| 10 | 0.1 |
| 11 | 0.2 |
| 12 | 0.6 |
| 13 | 1.0 |

TABLE 7

| | Phosphate buffers | |
|---|---|---|
| Buffer | Concentration NaCl (M) | Concentration $NaH_2PO_4$ (M) |
| 1 | 0.15 | 0.01 |
| 2 | 0.50 | 0.01 |
| 3 | 1.00 | 0.01 |
| 4 | 1.50 | 0.01 |

Nile Red (3.184 mg) was dissolved in a mixture of THF and acetone (50/50, 10 mL). This solution (10 µL) was incubated with each OSA-HA solution (10 mL) under stirring, overnight, in the dark and at room temperature. Each solution was analysed at 25° C. at an excitation wavelength of 543 nm whereas emission spectra were recorded from 580 to 700 nm. The excitation slit was set to 1 and the emission slit was adjusted for each solution. The intensity of the fluorescence emission (I) was plotted as a function of the wavelength (λ).

The wavelength corresponding to the maximum intensity (λ max) was determined by fitting the curve I vs. λ with a polynomial function of order 6. Each λ max value was the average of three measurements.

In order to determine the CAC, λ max was plotted as a function of the polymer concentration (C). The CAC was deduced at the inflexion point of the curve λ max vs. C (FIG. 10).

Figure 10:
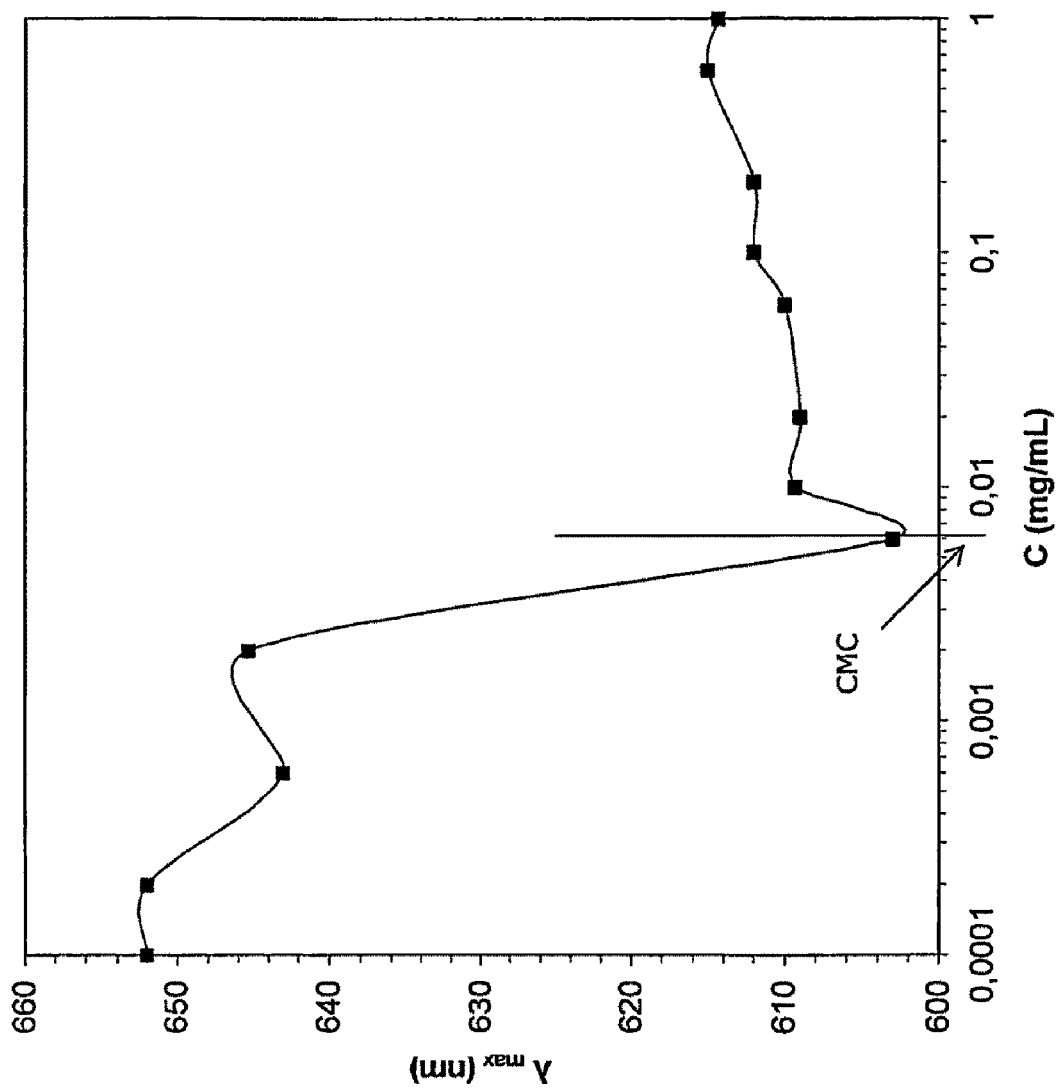
FIG. 10. Shows the wavelength of maximum emission as a function of OSA-HA (DS=44%) concentration in buffer 1 as described in Example 19.

In FIG. 10 the CAC of OSA-HA (DS= 44%) was somewhere between 0.003 and 0.004 mg/mL. This phenomenon was not observed for unmodified HA. Indeed fluorescence could not be detected at any HA concentrations which means that it was not possible to solubilize Nile Red in HA solutions. This evidences the presence of polymeric assemblies in OSA-HA solutions.

Example 20

Influence of the Salt Concentration on CAC of OSA-HA (DS=44%)

Figure 11:
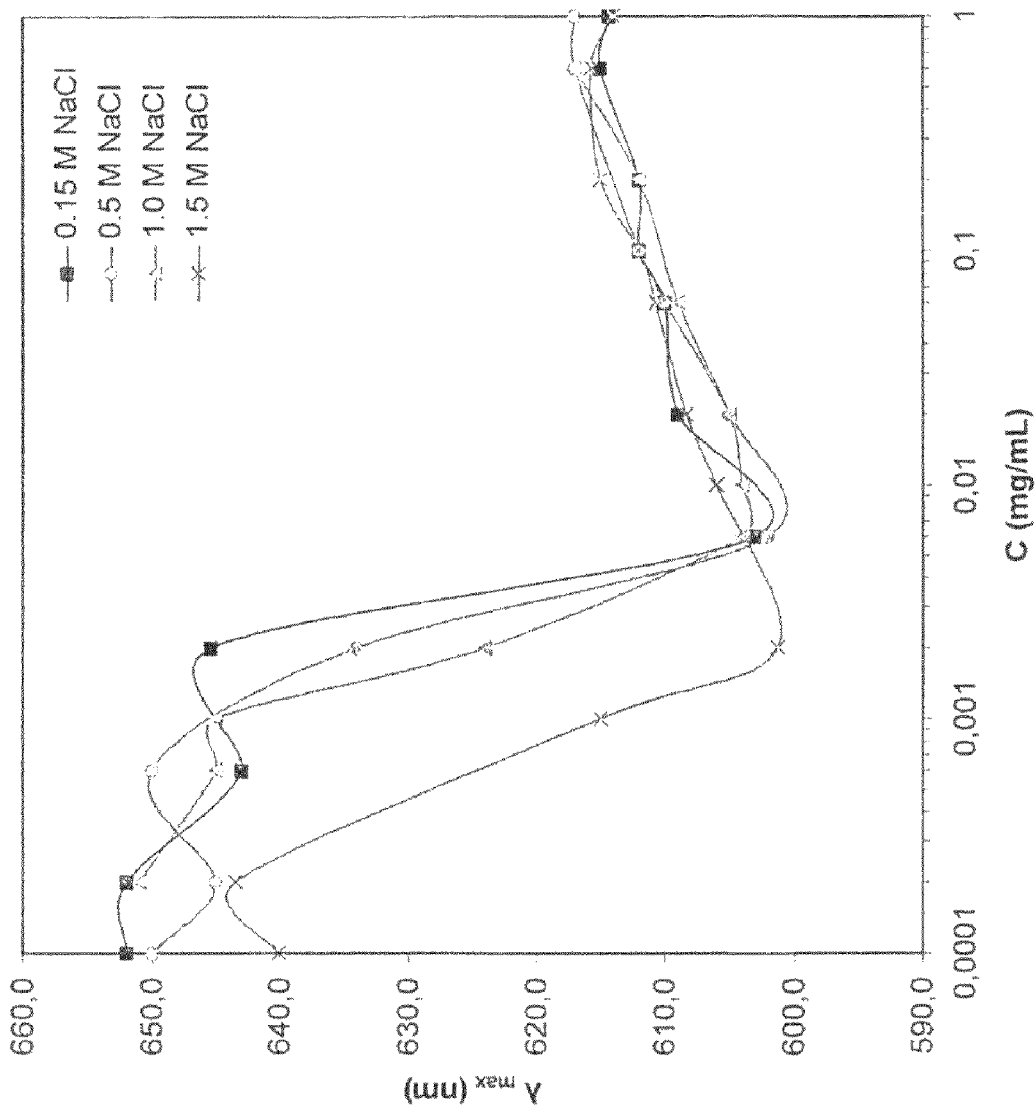
FIG. 11. Shows the wavelength of maximum emission as a function of OSA-HA (DS=44%) concentration, and that the CAC decreases as the concentration of NaCl increases, as described in Example 20.

The same experimental set-up as the one described in the previous example was used to study the influence of salt concentration on the value of CAC of OSA-HA (DS=44%). The results are shown in table 8 below as well as in FIG. 11.

TABLE 8

| Concentration of NaCl (M) | Onset of CAC (mg/mL) | Extend of the transition (mg/mL) | CAC (mg/mL) |
|---|---|---|---|
| 0.15 | 0.002 | 0.002-0.006 | 0.003-0.004 |
| 0.5 | 0.0006 | 0.0006-0.006 | 0.003 |
| 1.0 | 0.0006 | 0.0006-0.006 | 0.002 |
| 1.5 | 0.0002 | 0.0002-0.002 | 0.0006-0.0007 |

Example 21

Zeta Potential of OSA-HA (DS=44%) Polymeric Micelles

Figure 12:
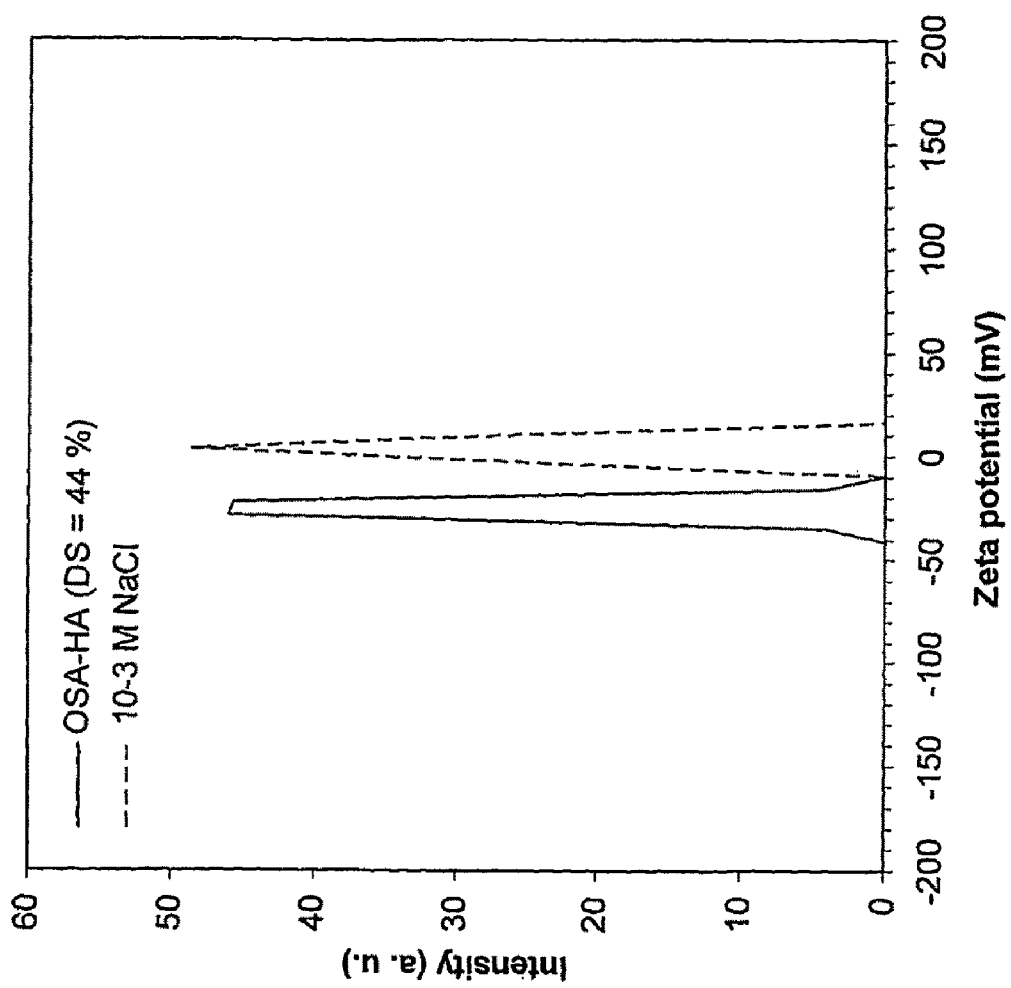
FIG. 12. Shows the Zeta potential of OSA-HA (DS=44%, 1 mg/mL) in 10-3 M NaCl as determined in Example 21.

The zeta potential of OSA-HA (DS=44%) polymeric micelles was determined by capillary electrophoresis (Zetasizer 3000 HS, Malvern, United Kingdom) coupled to a Doppler laser interferometer. Measurements were recorded at 25° C. OSA-HA was dissolved in 10-3 M NaCl (at a concentration of 1 mg/mL) prior to the measurement. The zeta potential of OSA-HA (DS=44%, 1 mg/mL in 10-3 M NaCl) was evaluated to approximately −25 mV (FIG. 12).

Example 22

Transmission Electron Microscopy of OSA-HA (DS=44%) Polymeric Micelles

Figure 13:
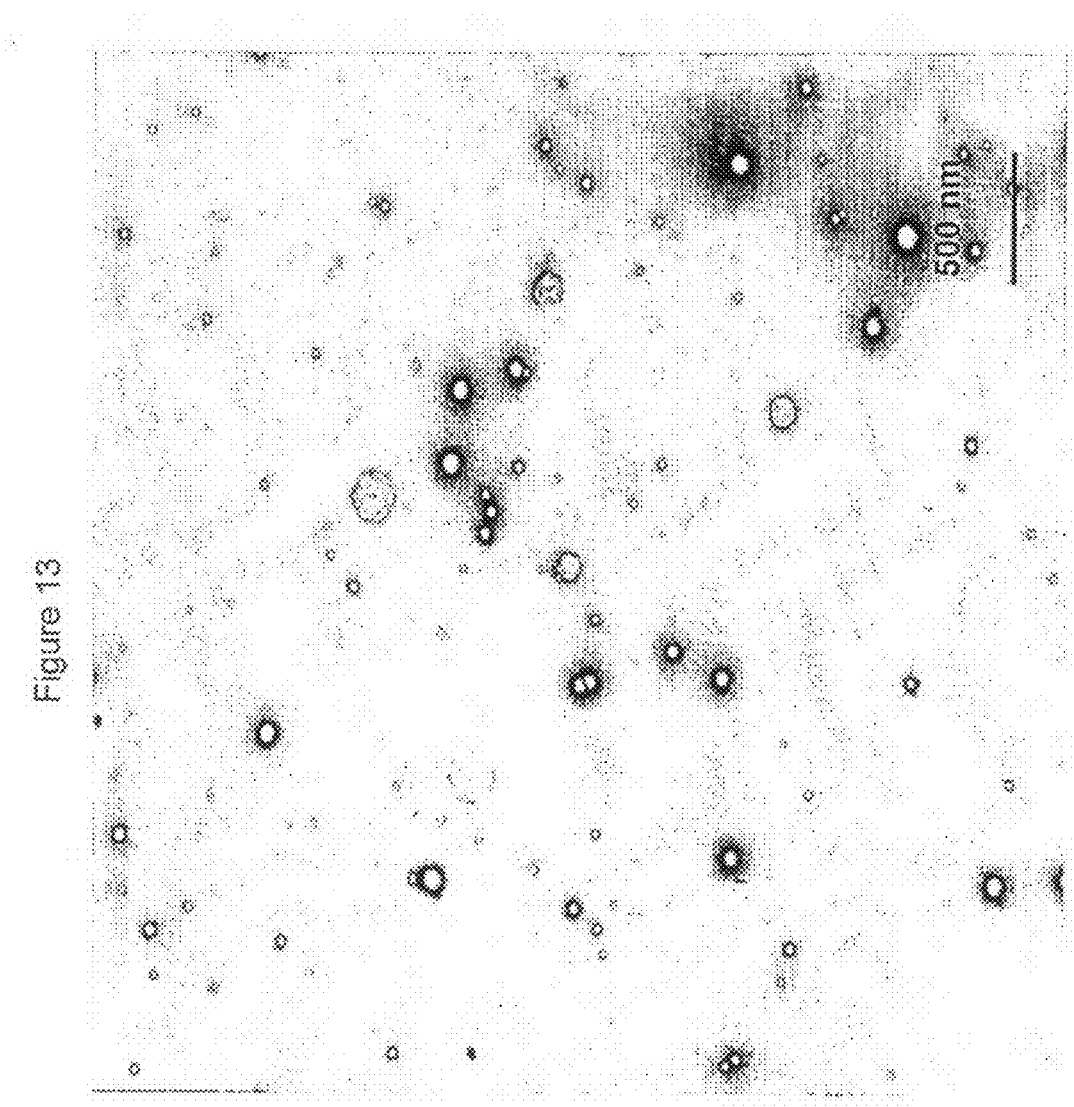
FIG. 13. Shows a transmission electron micrograph of OSA-HA (DS=44%) polymeric micelles from Example 22, that are spherical in shape and have submicronic dimensions typically from 50 to 200 nm.

Microscopic observations of OSA-HA (DS=44%) polymeric micelles were made with a transmission electron microscope (EM 410, Philips, The Netherlands). Samples were deposited on ionised carbon coated copper grids and stained with an aqueous uranyl acetate solution (2%). Microscopic snapshots clearly showed that the OSA-HA polymeric micelles are spherical in shape and have submicronic dimensions typically from 50 to 200 nm (data not shown). This is shown in FIG. 13.

The invention claimed is:

1. A hyaluronic acid derivative comprising n repeating units of formula (I):

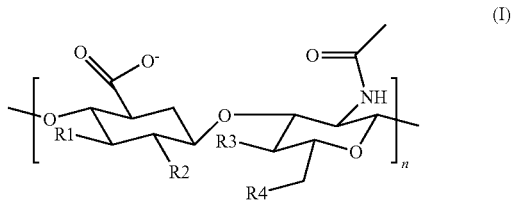

wherein
(a) in at least one repeating unit, one or more of the R1, R2, R3, and R4 groups is an aryl-succinic acid of formula (II):

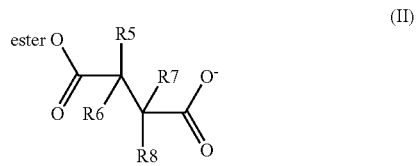

wherein at least one of the R5, R6, R7, and R8 groups is an aryl-group and the other R5, R6, R7, and R8 groups are hydrogen, and the oxygen labelled "ester" forms an ester bond with structure (I); and (b) in the other repeating units, the R1, R2, R3, and R4 groups are hydroxyl groups,.

2. The hyaluronic acid derivative of claim 1, wherein one of the R1, R2, R3, and R4 groups is an aryl-succinic acid of formula (II).

3. The hyaluronic acid derivative of claim 1, wherein two of the R1, R2, R3, and R4 groups are an aryl-succinic acid of formula (II).

4. The hyaluronic acid derivative of claim 1, wherein three of the R1, R2, R3, and R4 groups are an aryl-succinic acid of formula (II).

5. The hyaluronic acid derivative of claim 1, wherein at least one of the R1, R2, R3, and R4 groups is an aryl-succinic acid of formula (II), wherein the aryl group is phenyl.

6. The hyaluronic acid derivative of claim 5, wherein at least three of the R5, R6, R7, and R8 groups are an aryl group.

7. The hyaluronic acid derivative of claim 1, which has an average molecular weight of between 10,000 and 1,500,000 Da.

8. The hyaluronic acid derivative of claim 1, which has an average molecular weight of between 10,000 and 50,000 Da.

9. The hyaluronic acid derivative of claim 1, which has an average molecular weight of between 50,000 and 500,000 Da.

10. A composition comprising a hyaluronic acid derivative of claim 1 and a water soluble excipient.

11. The composition of claim 10, wherein the excipient is lactose.

12. A pharmaceutical composition comprising an effective amount of a hyaluronic acid derivative of claim 1 and a pharmaceutically acceptable carrier, excipient or diluent.

13. A cosmetic article comprising a hyaluronic acid derivative of claim 1.

14. A sanitary, medical or surgical article comprising a hyaluronic acid derivative of claim 1, which is a diaper, a sanitary towel, a surgical sponge, a wound healing sponge, or a part comprised in a band aid or other wound dressing material.

15. A medicament capsule, microcapsule, nanocapsules, microsphere or nanosphere comprising a hyaluronic acid derivative of claim 1.

* * * * *